(12) United States Patent
Dias

(10) Patent No.: US 6,540,791 B1
(45) Date of Patent: Apr. 1, 2003

(54) STABLE ALKALINE HAIR BLEACHING COMPOSITIONS AND METHOD FOR USE THEREOF

(75) Inventor: Louis Carlos Dias, Virginia Water (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/537,451

(22) Filed: Mar. 27, 2000

(51) Int. Cl.$^7$ .............................. D06L 3/04; D06L 3/00; A61K 7/13

(52) U.S. Cl. .................. 8/111; 8/405; 8/406; 8/407; 8/408; 8/102; 8/103; 8/101

(58) Field of Search .................. 8/405, 406, 407, 8/408, 101, 102, 103, 111

(56) References Cited

U.S. PATENT DOCUMENTS

| | | | |
|---|---|---|---|
| 3,997,659 A | * 12/1976 | Knohl et al. ............. | 424/62 |
| 4,027,008 A | 5/1977 | Sokol | |
| 4,327,751 A | * 5/1982 | Evans ....................... | 132/7 |
| 4,536,182 A | 8/1985 | Tatin ........................ | 8/107 |
| 5,116,388 A | * 5/1992 | Brooks ..................... | 8/405 |
| 5,560,750 A | * 10/1996 | Crews et al. ............ | 8/431 |
| 6,022,381 A | 2/2000 | Dias et al. ................ | 8/406 |
| 6,240,929 B1 | 6/2001 | Richard et al. | |
| 6,260,556 B1 | * 7/2001 | Legrand et al. .......... | 132/208 |

FOREIGN PATENT DOCUMENTS

| | | | |
|---|---|---|---|
| EP | 076166 B1 | 2/1987 | ............ C11D/1/83 |
| GB | 2072643 | 10/1981 | ......... C01B/15/037 |
| WO | 91/09807 | 7/1991 | ......... C01B/15/037 |
| WO | 93/13012 | 7/1993 | ......... C01B/15/037 |

OTHER PUBLICATIONS

U.S. application No. 09/537,452, Dias, filed Mar. 27, 2000.

* cited by examiner

*Primary Examiner*—Yogendra N. Gupta
*Assistant Examiner*—D G Hamlin
(74) *Attorney, Agent, or Firm*—Andrew A. Paul; Tara M. Rosnell; Steven W. Miller

(57) ABSTRACT

An alkaline hair bleaching composition comprising (a) from about 0.01% to about 12%, by weight, of at least one oxidizing agent; (b) from about 0.2% to about 20%, by weight, of a buffering system, present in an amount sufficient to generate a pH of the composition in the range from about 5 to about 11, wherein said buffering system comprises at least one pH modifying ingredient selected from the group consisting of (i) borates buffers, (ii) alkalizing agents, and mixtures thereof; (c) from about 150 ppm to about 5,000 ppm of at least one stabilizer; and (d) from about 0.01% to about 50%, by weight, of at least one hair care ingredient selected from the group consisting of (i) surfactants, (ii) catalysts, (iii) thickeners, (iv) conditioners, and mixtures thereof.

20 Claims, No Drawings

STABLE ALKALINE HAIR BLEACHING COMPOSITIONS AND METHOD FOR USE THEREOF

TECHNICAL FIELD OF THE INVENTION

This invention relates to stable alkaline hair bleaching compositions which provide improved performance of bleaching agents and increased shelf-life. These compositions contain: (a) an oxidizing agent; (b) a buffering system comprising a borates buffer and/or an alkalizing agent; (c) a stabilizer; and (d) at least one hair care ingredient selected from the group consisting of (i) surfactants, (ii) catalysts, (iii) thickeners, (iv) conditioners, and mixtures thereof. The invention further relates to stable alkaline compositions which provide both bleaching and coloring to the hair, to kits containing the above compositions, and to methods of using the above compositions.

BACKGROUND OF THE INVENTION

The desire to alter the color of human hair is not a facet of modem times. Since the days of the Roman Empire the color of human hair has been routinely altered to accommodate the changes of fashion, style, and simply personal preference. One aspect of this phenomenon is reflected in an adage in which reputedly "blondes have more fun." Another aspect is reflected in the noticeably colorful appearance of athletes' hair during competitions recently. However the attainment of precise initial colors which are retained by the hair for a desirable period, without undesirable side effects to the hair and skin, and producing a product with a longer shelf-life, have remained more elusive goals. This has been particularly difficult where lightening, or "bleaching," of the hair is desired.

The difficulties in the development of hair bleaching and coloring compositions which can deliver precise long-lasting colors are in part due to the inherent structure of the hair itself and in part due to the necessary conditions of effective hair coloration processes. Common difficulties with conventional hair bleaching and coloring compositions include color fade, wash fade, irregular dye uptake, hair damage and brittleness, skin irritation, odor and skin staining. In the case where the hair bleaching and coloring compositions contain oxidizers, these difficulties are compounded by the fact that the oxidizing agent which causes bleaching is typically stored at a low pH and then just prior to use by the consumer, it is mixed with either a high pH buffer or a high pH coloring solution or both. The oxidizer is stored at low pH until just prior to use to increase its stability as oxidizers at high pH tend to degrade quickly over time. This decomposition occurs during the period of distribution from the manufacturer to warehouses to retailers, and finally to consumers. When oxidizer solutions that have been at high pH for some time are applied to the hair, the bleaching effect is very poor.

Currently marketed oxidative hair bleaching products typically include an oxidizing agent, such as hydrogen peroxide, in a solution at low pH (about 4), and a buffering agent, such as ammonium hydroxide or monoethanolamine, in another solution, at high pH (about 10). The consumer mixes these solutions just prior to use and applies the resulting solution, having a pH of about 10, to the hair. The two solutions are stored at differing pH's in order to increase the shelf-life of the bleaching product. However, this results in an inconvenience to the consumer who must store these bottles in limited, and sometimes cramped bathroom storage space, and then mix these two solutions just prior to use. There are some marketed oxidative hair bleaching products which include an oxidizing agent, such as hydrogen peroxide, in a solution at low pH (about 4), in which the consumer sprays this solution onto the hair, and over a period of time, coupled with direct exposure to the sun, some lightening of the hair occurs. However, such products result in poor bleaching quality, and tend to only lighten the hair very little. A need exists for a single solution hair bleaching product that has a longer stable shelf-life and that provides excellent bleaching quality.

Currently marketed products which provide hair bleaching and coloring, combine hair lightening with hair coloring, and typically are of the type which includes either oxidative or non-oxidative hair dyes.

Those hair bleaching and coloring products which contain non-oxidative dyes typically do not include an oxidizing agent, but rather, include a pre-formed dye solution at alkaline pH. Lacking an oxidizer, such products tend to not be able to deliver good gray coverage or provide lightening. Thus, their shade palette is very limited. Up to now, an oxidizer has not been included at least in part because of the shelf-life degradation problems discussed above. Accordingly, a need exists for a single solution hair bleaching and coloring product that has a longer stable shelf-life and which will provide good gray coverage and provide quality lightening.

Those hair bleaching and coloring products which contain oxidative dyes typically include an oxidizing agent, such as hydrogen peroxide, in a solution at low pH (about 4), and a buffering agent, such as ammonium hydroxide or monoethanolamine, at high pH (about 10), with a dye solution which comprises precursor dye intermediates and coupler dye intermediates at high pH (about 10). The consumer mixes both of these solutions just prior to use and applies the resulting solution, having a pH of about 10, to the hair. The two solutions are stored at differing pH's in order to increase the shelf-life of the bleaching and coloring product, and also because introducing the oxidizing agent into the solution containing the dye intermediates is what initiates the formation of color between these intermediates. However, yet again this results in an inconvenience to the consumer who must store these bottles in limited, and sometimes cramped bathroom storage space, and then mix these three solutions just prior to use. A need exists for a hair bleaching and coloring product that has a longer stable shelf-life.

It would be desirable to employ alkaline solutions of oxidizing agents into hair bleaching and coloring products in order to enhance the performance of the oxidizer, to increase shelf-longevity, and to reduce the amount of time and storage space that a consumer must invest in attaining desired hair effects. A reduction in the number of individually bottled solutions necessary would also be desirable for a manufacturer, so as to reduce the cost of manufacturing and shipping, and for both warehousers and retailers, so as to reduce the amount of shelf space required for storage. These cost savings would inevitably be enjoyed by the consumer as well.

In GB 2,072,643 and EP 0,076,166B, Interox Chemicals, Ltd., describes a way to increase the stability of aqueous alkaline hydrogen peroxide solutions by employing an aminomethylene phosphonic acid together with a low weight alcohol, such as ethanol or iso-propanol as a stabilizer system, however, the presence of the alcohol inevitably reduces the flash point of the composition and introduces additional processing costs. The incorporation of certain aminomethylene phosphonic acids as stabilizers in alkaline hydrogen peroxide solutions has also been described in WO 91/09 807 (Interox).

During the transportation and storage of alkaline hydrogen peroxide solutions, there is a tendency for a downwards drift of the solutions' pH to occur. This may be counteracted to some degree by incorporating a buffer that is encompassed within the broad descriptive term "borates," because a mildly alkaline pH can thereby be maintained longer, however, processing difficulties have been encountered in the incorporation of certain borates. Atochem Company describes the incorporation of certain borate compounds together with a silicate as stabilizer in short-term alkaline hydrogen peroxide bleaching baths in EP 0,11 9,920B, however, such solutions are not suitable for distribution and sale to the general public because they have a much restricted shelf-life.

In WO 93/13 012, Interox describes a storage stable hydrogen peroxide solution which combines a certain borates buffer with a certain aminomethylene phosphonic acid stabilizer, however, this composition is not suitable for application to the hair for bleaching or coloring purposes, but rather is intended for use as a general purpose household bleach and disinfectant. Applicants have discovered stable alkaline formulations which provide for a single solution hair bleaching product, a single solution hair bleaching and coloring product, and hair bleaching and coloring product comprising only two solutions, wherein all of these products have increased shelf-longevity, and provide enhanced bleaching effects. Applicants have found that by incorporating oxidizing agents with a buffering system comprising certain borates buffers and/or alkalizing agents, and stabilizers, with certain hair care ingredients, stable hair bleaching and/or coloring compositions can be made which are safe and effective for use on mammalian hair and which provide the shelf-life and bleaching effect benefits mentioned above.

SUMMARY OF THE INVENTION

The present invention relates to stable alkaline hair bleaching compositions suitable for the treatment of mammalian hair. More specifically, the present invention relates to alkaline hair bleaching compositions comprising: (a) from about 0.01% to about 12%, by weight, of at least one oxidizing agent; (b) from about 0.2% to about 20%, by weight, of a buffering system, present in an amount sufficient to generate a pH of the composition in the range from about 5 to about 11, wherein the buffering system comprises at least one pH modifying ingredient selected from the group consisting of (i) borates buffers, (ii) alkalizing agents, and mixtures thereof; (c) from about 150 ppm to about 5,000 ppm of at least one stabilizer; and (d) from about 0.01% to about 50%, by weight, of at least one hair care ingredient selected from the group consisting of (i) surfactants, (ii) catalysts, (iii) thickeners, (iv) conditioners, and mixtures thereof.

In further embodiments, the present invention also relates to stable alkaline hair bleaching and coloring compositions, which further comprise coloring agents. The invention also relates to kits comprising stable alkaline hair bleaching and/or coloring compositions, and methods for use thereof.

DETAILED DESCRIPTION OF THE INVENTION

The stable alkaline hair bleaching compositions of the present invention provide for a single solution hair bleaching product, a single solution hair bleaching and coloring product, and hair bleaching and coloring product comprising only two solutions, wherein all of these products have increased shelf-longevity, and provide enhanced bleaching effects. The compositions are safe and effective for use on mammalian hair and provide the shelf-life and bleaching effect benefits mentioned above.

As used herein the term "hair" to be treated may be "living" i.e. on a living body or may be "non-living" i.e. in a wig, hairpiece or other aggregation of non-living fibers, such as though used in textiles and fabrics. Mammalian, preferably human hair is preferred, though animal hair, such as dog hair and cat hair are suitable. While the hair to be bleached and/or colored is typically located upon the head, it is contemplated that the inventive compositions described herein may be applied to hair located anywhere on the body, including, eyebrows, mustaches, beards, and anywhere else the consumer prefers. Wool, fur and other melanin-containing fibers or other keratinous fibers are also suitable substrates for the compositions according to the present invention, and are included within the definition of hair.

As used herein the term "hair bleaching composition" is used in the broad sense in that it is intended to encompass compositions containing the combinations herein of: (a) at least one oxidizing agent; (b) a buffering system comprising at least one pH modifying ingredient selected from the group consisting of (i) borates buffers, (ii) alkalizing agents, and mixtures thereof; (c) at least one stabilizer; and (d) at least one hair care ingredient selected from the group consisting of (i) surfactants, (ii) catalysts, (iii) thickeners, (iv) conditioners, and mixtures thereof. Moreover, it is also intended to include complex compositions which contain other components which may or may not be active ingredients. Thus, the term "hair bleaching composition" and also the term "hair bleaching and coloring composition" are intended to apply to compositions which contain additional ingredient commonly known and used in hair bleaching and coloring compositions as viscosity modifiers, conditioning enhancers, preservatives, perfumes, and ingredients used to modify aesthetics.

It is to be understood that the percentage weights of the composition components herein are expressed in terms of the total composition, and includes the composition in the form of intended use.

The components, including those which may optionally be added, of the stable alkaline hair bleaching compositions of the present invention, as well as methods for preparation, and methods of use, are described in detail below.

I. Components

The stable alkaline hair bleaching compositions of the present invention comprise: (a) at least one oxidizing agent; (b) a buffering system comprising at least one pH modifying ingredient selected from the group consisting of (i) borates buffers, (ii) alkalizing agents, and mixtures thereof; (c) at least one stabilizer; and (d) at least one hair care ingredient selected from the group consisting of (i) surfactants, (ii) catalysts, (iii) thickeners, (iv) conditioners, and mixtures thereof. Each of these ingredients is described in detail below.

A. Oxidizing Agent

The stable hair bleaching compositions of the present invention comprise as an essential feature, at least one oxidizing agent, which may be an inorganic or organic oxidizing agent. The oxidizing agent is preferably present at a level from about 0.01% to about 12%, by weight of the composition, preferably from about 0.01% to about 10%, more preferably from about 1% to about 6%. Such oxidizing agent(s) should be physically and chemically compatible with the essential components of the composition, and should not otherwise unduly impair product stability, aesthetics or performance.

1. Inorganic Oxidizing Agents

A preferred oxidizing agent for use herein is an inorganic peroxygen oxidizing agent. The inorganic peroxygen oxidizing agent should be safe and effective for use in the compositions herein. Preferably, the inorganic peroxygen oxidizing agents suitable for use herein will be soluble in the compositions according to the present invention when in liquid form or in the form intended to be used. Preferably, inorganic peroxygen oxidizing agents suitable for use herein will be water-soluble, meaning such agents which have a solubility to the extent of about 10 g in 1000 ml of deionized water at 25° C. ("Chemistry" C. E. Mortimer. 5th ed. at page 277).

The inorganic peroxygen oxidizing agents useful herein are generally inorganic peroxygen materials capable of yielding peroxide in an aqueous solution. Inorganic peroxygen oxidizing agents are well known in the art and include hydrogen peroxide, inorganic alkali metal peroxides such as sodium periodate, sodium perbromate and sodium peroxide, and inorganic perhydrate salt oxidizing compounds, such as the alkali metal salts of perborates, percarbonates, perphosphates, persilicates, persulfates and the like. These inorganic perhydrate salts may be incorporated as monohydrates, tetrahydrates etc. Mixtures of two or more of such inorganic peroxygen oxidizing agents can be used if desired. While alkali metal bromates and iodates are suitable for use herein the bromates are preferred. Highly preferred for use in the compositions according to the present invention is hydrogen peroxide.

It has been found that by using the compositions of the present invention, it is possible to deliver effective hair bleaching by employing alkaline formulations in order to enhance the performance of hydrogen peroxide or other suitable oxidizing agent.

In preferred compositions according to the present invention the inorganic peroxygen oxidizing agent is present at a level from about 0.01% to about 12%, by weight of the composition, preferably from about 0.01% to about 10%, more preferably from about 1% to about 6%, and still more preferably from about 2% to about 4%.

2. Organic Oxidizing Agents

The compositions according to the present invention may instead or in addition to the inorganic peroxygen oxidizing agent(s) described above, comprise one or more pre-formed organic peroxyacid oxidizing agents.

Suitable organic peroxyacid oxidizing agents for use in the coloring compositions according to the present invention conform to the general formula (I):

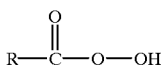

wherein R is selected from saturated or unsaturated, substituted or unsubstituted, straight or branched chain, alkyl, aryl or alkaryl groups having from 1 to 14 carbon atoms.

A class of organic peroxyacid compounds suitable for use herein are the amide substituted compounds of the following general formulae (II) or (III):

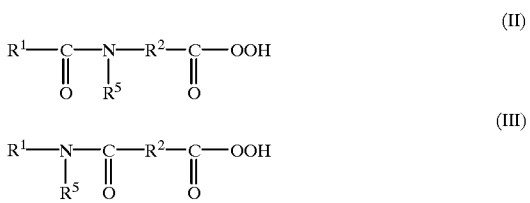

wherein $R^1$ is, a saturated or unsaturated alkyl or alkaryl group, or an aryl group, having from 1 to 14 carbon atoms, $R^2$ is, a saturated or unsaturated alkyl or alkaryl group, or an aryl group, having from 1 to 14 carbon atoms, and $R^5$ is H or, a saturated or unsaturated alkyl or alkaryl group, or an aryl group, having from 1 to 10 carbon atoms. Amide substituted organic peroxyacid compounds of this type are described in EP-A-0,170,386, which description is incorporated herein by reference.

Other suitable organic peroxyacid oxidizing agents include peracetic, pernanoic, nonylamidoperoxycaproic acid (NAPCA), perbenzoic, m-chloroperbenzoic, di-peroxyisophthalic, mono-peroxyphthalic, peroxylauric, hexanesulphonyl peroxy propionic, N,N-phthaloylamino peroxycaproic, monoper succinic, nonanoyloxybenzoic, dodecanedioylmonoperoxybenzoic, nonylamide of peroxyadipic acid, diacyl and tetraacylperoxides, especially diperoxydodecanedioic acid, diperoxytetradecanedioic acid and diperoxyhexadecanedioic acid and derivatives thereof. Mono- and di-perazelaic acid, mono- and di-perbrassylic acid and N-phthaloylaminoperoxicaproic acid and derivatives thereof are also suitable for use herein. The preferred peroxyacid materials suitable for use herein are selected from peracetic and pernanoic acids and mixtures thereof.

The preformed organic peroxyacid oxidizing agents should be safe and effective for use in the compositions herein. Preferably, the preformed organic peroxyacid oxidizing agents suitable for use herein will be soluble in the compositions according to the present invention when in liquid form and in the form intended to be used. Preferably, organic peroxyacid oxidizing agents suitable for use herein will be water-soluble, meaning such agents which have a solubility to the extent of about 10 g in 1000 ml of deionized water at 25° C. ("Chemistry" C. E. Mortimer. 5th ed. at page 277).

The preformed organic peroxyacid oxidizing agent, where present, is preferably present at a level from about 0.01% to about 8%, by weight of the composition, more preferably from about 0.1% to about 6%, yet more preferably from about 0.2% to about 4%, and still yet more preferably from about 0.3% to about 3%.

When both an inorganic peroxygen oxidizing agent and a preformed organic peroxy acid are present in the compositions herein, the weight ratio of the inorganic peroxygen oxidizing agent to the preformed organic peroxy acid is preferably in the range from about 0.0125:1 to about 500:1, more preferably from about 0.0125:1 to about 50:1.

In addition to the inorganic peroxygen oxidizing agents and the preformed organic peroxyacid oxidizing agents suitable for use herein, the compositions according to the present invention may optionally comprise additional organic peroxides such as urea peroxide, melamine peroxide and mixtures thereof. The level of such additional organic peroxides, where present, is from about 0.01% to about 3%, by weight of the composition, preferably from about 0.01% to about 2%, more preferably from about 0.1% to about 1.5% and most preferably from about 0.2% to about 1%.

B. Buffering System

The stable alkaline hair bleaching compositions of the present invention comprise, as an essential feature, from about 0.2% to about 20%, by weight of the composition, of a buffering system, present in an amount sufficient to generate a pH of the composition in the range from about 5 to about 11, wherein the buffering system comprises at least one pH modifying ingredient selected A. from the group consisting of (i) borates buffers, (ii) alkalizing agents, and mixtures thereof. Such buffering system should be physically and chemically compatible with the essential components of the composition, and should not otherwise unduly impair product stability, aesthetics or performance.

1. Borates Buffer

The buffering system of the stable alkaline hair bleaching compositions of the present invention may comprises a borates buffer. The borates buffer may be of any well known water soluble alkali metal and ammonium borate, such as the sodium borates and potassium borates. Non-limiting examples of such alkali metal borates include, sodium tetraborate pentahydrate, sodium tetraborate decahydrate, sodium perborate monohydrate, sodium perborate tetrahydrate, sodium metaborate tetrahydrate, potassium tetraborate pentahydrate, potassium tetraborate decahydrate, potassium perborate monohydrate, potassium perborate tetrahydrate, and potassium metaborate tetrahydrate. Ammonium borates, such as the alkanol ammonium borates, may also be used in the compositions herein, preferably those having from 2 to 9 carbon atoms. A preferred borates buffer is sodium tetraborate decahydrate. When sodium tetraborate decahydrate is present, it is typically in an amount from about 0.1% to about 5%, by weight of the composition, more preferably from about 0.2% to about 1%.

2. Alkalizing Agent

The buffering system of the stable alkaline hair bleaching compositions of the present invention may also comprise an alkalizing agent to adjust the pH to the desired level, typically from about 5 to about 11. The alkalizing agent, when present, may typically be at an amount from about 0.1% to about 20%, by weight, of the composition, preferably from about 0.1% to about 15%. Some alkalizing agents, such as ammonium hydroxide and monoethylamine (MEA), are known to act as hair swelling agents (HSA's).

Non-limiting examples of suitable alkalizing agents for use in the compositions herein are: ammonia; alkyl amines, such as ethylamine and tri-ethylamine; alkanolamines, such as mono-, di-, and tri-ethanolamine; ammonia derivatives; hydroxides of sodium or potassium; carbonates of sodium or potassium; ammonium hydroxide; ethylamine; dipropylamine; triethylamine; alkanediamines, such as 1,3-diaminopropane; anhydrous alkaline alkanolamines, such as mono- or di-ethanolamine, preferably those which are completely substituted on the amine group, such as dimethylaminoethanol; polyalkylene polyamines, such as diethylenetriamine; heterocyclic amines, such as morpholine; hydroxides of alkali metals, such as sodium and potassium hydroxide; hydroxides of alkali earth metals, such as magnesium and calcium hydroxide; basic amino acids such as L-arginine, lysine, oxy-lysine and histidine; and mixtures thereof. Also suitable for use herein are compounds that form $HCO_3^-$ by dissociation in water. Several compounds which produce $HCO_3^-$ ions are described in EP-A-435,012, which description is incorporated herein by reference, including: $Na_2CO_3$, $NaHCO_3$, $K_2CO_3$, $KHCO_3$, $(NH_4)_2CO_3$, $NH_{4H}CO_3$, $CaCO_3$ and $Ca(HCO_3^-)_2$.

Preferred alkalizing agents for use herein include: ammonium hydroxide, monoethanolamine (MEA), ammonium carbonate, ammonium hydrogen carbonate, sodium hydroxide and mixtures thereof.

C. Stabilizer

The stable alkaline hair bleaching compositions of the present invention comprise, as an essential component, from about 150 ppm to about 5,000 ppm of at least one stabilizer, preferably from about 150 ppm to about 1,500 ppm. Such stabilizer(s) should be physically and chemically compatible with the essential components of the composition, and should not otherwise unduly impair product stability, aesthetics or performance. While it is contemplated that any stabilizer known in the art may be used herein, a preferred class of stabilizers are heavy metal ion sequestrants.

1. Heavy Metal Ion Sequestrants

The stable alkaline hair bleaching compositions of the present invention may contain at least one heavy metal ion sequestrant. By heavy metal ion sequestrant it is meant herein components which act to sequester (chelate or scavenge) heavy metal ions. These components may also have calcium and magnesium chelation capacity, but preferentially they show selectivity to binding heavy metal ions, such as iron, manganese and copper. Such sequestering agents are valuable in hair bleaching and coloring compositions as herein described for the delivery of controlled oxidizing action as well as for the provision of good storage stability of the hair coloring products. The heavy metal ion sequestering agents of the present invention may be used in the form of their alkali metal salts, alkaline earth metal salts, ammonium salts, or substituted ammonium salts.

Suitable sequestering agents for use herein include: amino phosphonates; available as Dequest® from Monsanto; nitriloacetates; hydroxyethyl-ethylene triamines; organic phosphonates, such as amino-alkylene-poly-(alkylene phosphonates); alkali metal ethane 1-hydroxy disphosphonates; nitrilo trimethylene phosphonates; polycarboxylates, amino polycarboxylates, polyphosphonates, amino polyphosphonates and mixtures thereof.

Preferred among the above species are diethylene triamine penta (methylene phosphonate), ethylene diamine tri (methylene phosphonate) hexamethylene diamine tetra (methylene phosphonate) and hydroxy-ethylene 1,1 diphosphonate. A highly preferred class of stabilizers are aminomethylene phosphonic acids, such as cyclohexane-1,2-diaminotetrakis phosphonic acid (CDTMPA).

Preferred biodegradable non-phosphorous heavy metal ion sequestrants suitable for use herein include nitrilotriacetic acid and polyaminocarboxylic acids such as ethylenediaminetetracetic acid, ethylenetriamine pentaacetic acid, ethylenediamine disuccinic acid, ethylenediamine diglutaric acid, 2-hydroxypropylenediamine disuccinic acid or any salts thereof. Especially preferred is ethylenediamine-N,N'-disuccinic acid (EDDS) (described by Procter & Gamble in U.S. Pat. No. 4,704,233, which is incorporated herein by reference in its entirety).

Other suitable heavy metal ion sequestrants for use herein are iminodiacetic acid derivatives such as 2-hydroxyethyl diacetic acid or glyceryl imino diacetic acid, described in EP-A-317,542 and EP-A-399,133, which descriptions are incorporated herein by reference. The iminodiacetic acid-N-2-hydroxypropyl sulfonic acid and aspartic acid N-carboxymethyl N-2-hydroxypropyl-3-sulfonic acid sequestrants described in EP-A-516,102 (which description is incorporated herein by reference) are also suitable herein. Also suitable, are the β-alanine-N,N'-diacetic acid, aspartic acid-N,N'-diacetic acid, aspartic acid-N-monoacetic acid and iminodisuccinic acid sequestrants described in EP-A-509,382, which description is herein incorporated by reference.

Glycinamide-N,N'-disuccinic acid (GADS), ethylenediamine-N-N'-diglutaric acid (EDDG) and 2-hydroxypropylenediamine-N-N'-disuccinic acid (HPDDS) are also suitable, as are those sequestrants described in EP-A-476,257 (amino based sequestrants), EP-A-510,331 (sequestrants derived from collagen, keratin or casein), and EP-A-528,859 (alkyl iminodiacetic acid sequestrant), all of which descriptions are incorporated herein by reference. Dipicolinic acid and 2-phosphonobutane-1,2,4-tricarboxylic acid are also suitable.

Non-limiting examples of preferred combinations of heavy metal ion sequestering agents for use herein include (a) sodium stannate, etidronic acid, and pentasodium pentatate, (b) sodium stannate, disodium pyrophosphate, sodium pentatate, (c) sodium stannate, disodium pyrophosphate and EDTA, (d) sodium stannate, etidronic acid and EDTA and (e) sodium stannate, disodium pyrophosphate and etidronic acid.

Also useful in the compositions herein are the heavy metal ion sequestrants which comprise an alkoxylated benzoic acid or a salt thereof. The alkoxylated benzoic acid or the salt thereof conforms to the general formula (IV):

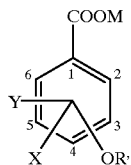

wherein X and Y are independently selected from —H, or —OR' (wherein R' is independently selected from $C_1$ to $C_{20}$ linear or branched alkyl chains, preferably R' is independently selected from $C_1$ to $C_5$ linear or branched alkyl chains, more preferably R' is —$CH_3$); and M is —H, a cation, or a cationic moiety, preferably M is —H, an alkali metal ion, or an alkaline earth metal ion, more preferably M is —H, —$Na^+$, or —$K^+$, and still yet more preferably M is —H.

D. Hair Care Ingredient

The stable alkaline hair bleaching compositions of the present invention comprise, as an essential component, from about 0.01% to about 50%, by weight, of at least one hair care ingredient selected from the group consisting of (i) surfactants, (ii) catalysts, (iii) thickeners, (iv) conditioning agents, and mixtures thereof. Such hair care ingredient(s) should be physically and chemically compatible with the essential components of the composition, and should not otherwise unduly impair product stability, aesthetics or performance.

1. Surfactants

The stable alkaline hair bleaching compositions of the present invention may contain a surfactant system. Suitable surfactants for inclusion in the compositions of the invention generally have a lipophilic chain length of from about 8 to about 22 carbon atoms and can be selected from anionic, nonionic, amphoteric, zwitterionic, cationic surfactants and mixtures thereof.

a. Anionic Surfactants

Anionic surfactants suitable for inclusion in the compositions of the present invention include alkyl sulphates, ethoxylated alkyl sulphates, alkyl glyceryl ether sulfonates, methyl acyl taurates, fatty acyl glycinates, N-acyl glutamates, acyl isethionates, alkyl sulfosuccinates, alkyl ethoxysulphosuccinates, alpha-sulfonated fatty acids, their salts and/or their esters, alkyl ethoxy carboxylates, alkyl phosphate esters, ethoxylated alkyl phosphate esters, alkyl sulphates, acyl sarcosinates and fatty acid/protein condensates, and mixtures thereof. Alkyl and/or acyl chain lengths for these surfactants are $C_{12}$ to $C_{22}$, preferably $C_{12}$ to $C_{18}$ more preferably $C_{12}$ to $C_{14}$.

b. Nonionic Surfactants

The compositions of the invention may also comprise water-soluble nonionic surfactant(s). Surfactants of this class include $C_{12}$ to $C_{14}$ fatty acid mono-and di-ethanolamides, sucrose polyester surfactants and polyhydroxy fatty acid amide surfactants having the general formula (V):

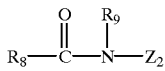

The preferred N-alkyl, N-alkoxy or N-aryloxy, polyhydroxy fatty acid amide surfactants according to the above formula are those in which $R_8$ is $C_5$ to $C_{31}$ hydrocarbyl, preferably $C_6$ to $C_{19}$ hydrocarbyl, including straight-chain and branched chain alkyl and alkenyl, or mixtures thereof and $R_9$ is typically hydrogen, $C_1$ to $C_8$ alkyl or hydroxyalkyl, preferably methyl, or a group of formula —$R^1$—O—$R^2$ (wherein $R^1$ is $C_2$ to $C_8$ hydrocarbyl including straight-chain, branched-chain and cyclic (including aryl), and is preferably $C_2$ to $C_4$ alkylene, $R^2$ is $C_1$ to $C_8$ straight-chain, branched-chain and cyclic hydrocarbyl including aryl and oxyhydrocarbyl, and is preferably $C_1$ to $C_4$ alkyl, especially methyl, or phenyl)). $Z_2$ is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. $Z_2$ preferably will be derived from a reducing sugar in a reductive amination reaction, more preferably $Z_2$ is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilised as well as the individual sugars listed above. These corn syrups may yield a mix of sugar components for $Z_2$. It should be understood that it is by no means intended to exclude other suitable raw materials. $Z_2$ preferably will be selected from the group consisting of —$CH_2$—$(CHOH)_n$—$CH_2OH$, —$CH(CH_2OH)$—$(CHOH)_{n-1}$—$CH_2H$, $CH_2(CHOH)_2(CHOR')$$CHOH)$—$CH_2OH$, wherein n is an integer from 1 to 5, inclusive, and R' is H or a cyclic mono- or polysaccharide, and alkoxylated derivatives thereof. As noted, most preferred are glycityls wherein n is 4, particularly —$CH_2$—$(CHOH)_4$—$CH_2OH$.

A highly preferred polyhydroxy fatty acid amide has the formula $R_8(CO)N$—$(CH_3)CH_2(CHOH)_4CH_2OH$ wherein $R_8$ is a $C_6$ to $C_{19}$ straight chain alkyl or alkenyl group. In compounds of the above formula, $R_8$—CO—N— can be, for example, cocoamide, stearamide, oleamide, lauramide, myristamide, capricamide, palmiamide, tallowamide, and the like.

Suitable oil derived nonionic surfactants for use herein include water soluble vegetable and animal-derived emollients such as triglycerides with a polyethylene glycol chain inserted; ethoxylated mono- and di-glycerides, polyethoxylated lanolins and ethoxylated butter derivatives. One preferred class of oil-derived nonionic surfactants for use herein have the general formula below (VI):

wherein n is from about 5 to about 200, preferably from about 20 to about 100, more preferably from about 30 to about 85, and wherein R comprises an aliphatic radical having on average from about 5 to 20 carbon atoms, preferably from about 7 to 18 carbon atoms.

Suitable ethoxylated oils and fats of this class include polyethyleneglycol derivatives of glyceryl cocoate, glyceryl caproate, glyceryl caprylate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil, preferably glyceryl tallowate and glyceryl cocoate.

Preferred for use herein are polyethylene glycol based polyethoxylated $C_9$–$C_{15}$ fatty alcohol nonionic surfactants containing an average of from about 5 to about 50 ethyleneoxy moieties per mole of surfactant.

Suitable polyethylene glycol based polyethoxylated $C_9$–$C_{15}$ fatty alcohols suitable for use herein include $C_9$–$C_{11}$ Pareth-3, $C_9$–$C_{11}$ Pareth-4, $C_9$–$C_{11}$ Pareth-5, $C_9$–$C_{11}$ Pareth-6, $C_9$–$C_{11}$ Pareth-7, $C_9$–$C_{11}$ Pareth-8, $C_{11}$–$C_{15}$ Pareth-3, $C_{11}$–$C_{15}$ Pareth-4, $C_{11}$–$C_{15}$ Pareth-5, $C_{11}$–$C_{15}$ Pareth-6, $C_{11}$–$C_{15}$ Pareth-7, $C_{11}$–$C_{15}$ Pareth-8, $C_{11}$–$C_{15}$ Pareth-9, $C_{11}$–$C_{15}$ Pareth-10, $C_{11}$–$C_{15}$ Pareth-11, $C_{11}$–$C_{15}$ Pareth-12, $C_{11}$–$C_{15}$ Pareth-13 and $C_{11}$–$C_{15}$ Pareth-14. PEG 40 hydrogenated castor oil is commercially available under the tradename Cremophor from BASF. PEG 7 glyceryl cocoate and PEG 20 glyceryl laurate are commercially available from Henkel under the tradenames Cetiol® HE and Lamacit® GML 20, respectively. $C_9$–$C_{11}$ Pareth-8 is commercially available from Shell, Ltd., under the tradename Dobanol® 91-8. Particularly preferred for use herein are polyethylene glycol ethers of ceteryl alcohol such as Ceteareth 25 which is available from BASF under the trade name Cremaphor® A25.

Also suitable for use herein are nonionic surfactants derived from composite vegetable fats extracted from the fruit of the Shea Tree (Butyrospermum Karkii Kotschy) and derivatives thereof. Similarly, ethoxylated derivatives of mango, cocoa and illipe butter may be used in compositions according to the invention. Although these are generally classified as ethoxylated nonionic surfactants, it is understood that a certain proportion may remain as non-ethoxylated vegetable oil or fat.

Other suitable oil-derived nonionic surfactants include ethoxylated derivatives of almond oil, peanut oil, rice bran oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil.

c. Amphoteric Surfactants

Amphoteric surfactants suitable for use in the compositions of the invention include:

(i) imidazolinium surfactants of the general formula (VII):

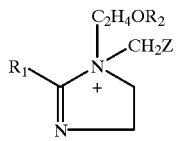

wherein $R_1$ is $C_7$–$C_{22}$ alkyl or alkenyl, $R_2$ is hydrogen or $CH_2Z$, each Z is independently $CO_2M$ or $CH_2CO_2M$, and M is H, alkali metal, alkaline earth metal, ammonium or alkanolammonium; and/or ammonium derivatives of general formula (VIII):

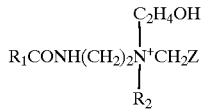

wherein $R_1$, $R_2$ and Z are as defined above;

(ii) aminoalkanoates of general formula (IX):

iminodialkanoates of the general formula (X):

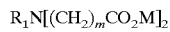

and iminopolyalkanoates of the general formula (XI):

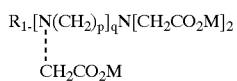

wherein n, m, p, and q are numbers from 1 to 4, and $R_1$ and M are independently selected from the groups specified above; and (iii) mixtures thereof.

Suitable amphoteric surfactants of type (i) above are marketed under the tradenames Miranol® and Empigen® and are understood to comprise a complex mixture of species. Traditionally, the Miranols have been described as having the general formula (VII), although the CTFA Cosmetic Ingredient Dictionary, 3rd ed. indicates the non-cyclic structure (VIII) while the 4th ed. indicates yet another structural isomer in which $R_2$ is O-linked rather than N-linked. In practice, a complex mixture of cyclic and non-cyclic species is likely to exist and both definitions are given here for sake of completeness. Preferred for use herein, however, are the non-cyclic species.

Examples of suitable amphoteric surfactants of type (i) include compounds of formula VII and/or VIII in which $R_1$ is $C_8H_{17}$ (especially iso-capryl), $C_9H_{19}$ and $C_{11}H_{23}$ alkyl. Especially preferred are the compounds in which $R_1$ is $C_9H_{19}$, Z is $CO_2M$ and $R_2$ is H; the compounds in which $R_1$ is $C_{11}H_{23}$, Z is $CO_2M$ and $R_2$ is $CH_2CO_2M$; and the compounds in which $R_1$ is $C_{11}H_{23}$, Z is $CO_2M$ and $R_2$ is H.

In CTFA nomenclature, materials suitable for use in the present invention include cocoamphocarboxypropionate, cocoamphocarboxy propionic acid, and especially cocoamphoacetate and cocoamphodiacetate (otherwise referred to as cocoamphocarboxyglycinate). Specific commercial products include those sold under the tradenames of Ampholak® 7TX (sodium carboxy methyl tallow polypropyl amine), Empigen® CDL60 and CDR 60 (Albright & Wilson), Miranol® H2M Conc., Miranol® C2M Conc. N.P., Miranol® C2M Conc. O.P., Miranol® C2M SF, Miranol® CM Special (Rhône-Poulenc); Alkateric® 2CIB (Alkaril Chemicals); Amphoterge® W-2 (Lonza, Inc.); Monateric® CDX-38, Monateric CSH-32 (Mona Industries); Rewoteric® AM-2C (Rewo Chemical Group); and Schercotic® MS-2 (Scher Chemicals). Further examples of amphoteric surfactants suitable for use herein include Octoxynol®-1, polyoxyethylene (1) octylphenyl ether; Nonoxynol®-4, polyoxyethylene (4) nonylphenyl ether and Nonoxynol®-9, polyoxyethylene (9) nonylphenyl ether.

It will be understood that a number of commercially-available amphoteric surfactants of this type are manufactured and sold in the form of electroneutral complexes with, for example, hydroxide counterions or with anionic sulfate or sulfonate surfactants, especially those of the sulfated $C_8$–$C_{18}$ alcohol, $C_8$–$C_{18}$ ethoxylated alcohol or $C_8$–$C_{18}$ acyl glyceride types. Furthermore, the concentrations and weight ratios of the amphoteric surfactants are based herein on the uncomplexed forms of the surfactants, any anionic surfactant counterions being considered as part of the overall anionic surfactant component content.

Examples of preferred amphoteric surfactants of type (ii) above, include N-alkyl polytrimethylene, poly-carboxymethylamines sold under the tradenames Ampholak® X07 and Ampholak® 7CX by Berol Nobel and also salts, especially the triethanolammonium salts and salts of N-lauryl-beta-amino propionic acid and N-lauryl-imino-dipropionic acid. Such materials are sold under the tradenames Deriphat® by Henkel and Mirataine® by Rhône-Poulenc.

d. Zwitterionic Surfactants

Water-soluble auxiliary zwitterionic surfactants suitable for inclusion in the compositions of the present invention include alkyl betaines of the formula $R_5R_6R_7N^+(CH_2)_nCO_2M$ and amido betaines of the general formula (XII) below,

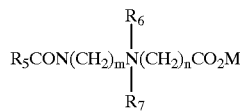

wherein $R_5$ is $C_{11}$–$C_{22}$ alkyl or alkenyl, $R_6$ and $R_7$ are independently $C_{1–C_3}$ alkyl, M is H, alkali metal, alkaline earth metal, ammonium or alkanolammonium, and n, m are each numbers from 1 to 4. Preferred betaines include cocoamidopropyldimethylcarboxymethyl betaine, laurylamidopropyldimethylcarboxymethyl betaine and Tego® betaine.

Water-soluble auxiliary sultaine surfactants suitable for inclusion in the compositions of the present invention include alkyl sultaines of the general formula (XIII) below:

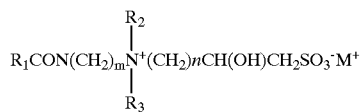

wherein $R_1$ is $C_7$ to $C_{22}$ alkyl or alkenyl, $R_2$ and $R_3$ are independently $C_1$ to $C_3$ alkyl, M is H, alkali metal, alkaline earth metal, ammonium or alkanolammonium and m and n are numbers from 1 to 4. Preferred for use herein is cocoamidopropylhydroxysultaine.

Water-soluble auxiliary amine oxide surfactants suitable for inclusion in the compositions of the present invention include alkyl amine oxide $R_5R_6R_7NO$ and amido amine oxides of the general formula (XIV) below:

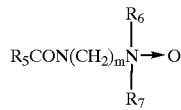

wherein $R_5$ is $C_{11}$ to $C_{22}$ alkyl or alkenyl, $R_6$ and $R_7$ are independently $C_1$ to $C_3$ alkyl, and m is a number from 1 to 4. Preferred amine oxides include cocoamidopropylamine oxide, lauryl dimethyl amine oxide and myristyl dimethyl amine oxide.

e. Cationic Surfactants

The compositions of the invention may also comprise water-soluble cationic surfactant(s). Such surfactants are described in *Surfactant Encyclopedia*, Martin Reiger, (published by Cosmetics and Toiletries, ISBN 0-931710-29-4), which description is incorporated herein by reference.

2. Catalyst

The stable alkaline hair bleaching compositions herein may contain a transition metal containing catalyst for the inorganic peroxygen oxidizing agents and, when present, the preformed peroxyacid oxidizing agent(s). One suitable type of catalyst is a catalyst system comprising a heavy metal cation of defined bleach catalytic activity, such as copper, iron or manganese cations, an auxiliary metal cation having little or no bleach catalytic activity, such as zinc or aluminium cations, and a sequestrant having defined stability constants for the catalytic and auxiliary metal cations, particularly ethylenediaminetetraacetic acid, ethylenediamine-tetra (methylenephosphonic acid) and water-soluble salts thereof. Such catalysts are disclosed by the Procter & Gamble Company in U.S. Pat. No. 4,430,243, which is incorporated herein by reference in its entirety.

Other types of suitable catalysts include the manganese-based complexes disclosed in U.S. Pat. Nos. 5,246,621 and 5,244,594, which descriptions are incorporated herein by reference. Preferred examples of these catalysts include $Mn^{IV}_2(u-O)_3(1,4,7$-trimethyl-1,4,7-triaza-cyclononane$)_2$-$(PF_6)_2$, $Mn^{III}_2(u-O)_1(u-OAc)_2(1,4,7$-tri-methyl-1,4,7-triazacyclo-nonane$)_2$-$(ClO_4)_2$, $Mn^{IV}_4(u-O)_6(1,4,7$-triazacyclononane$)_4$-$(ClO_4)_2$, $Mn^{III}Mn^{IV}_4(u-O_1(u-OAc)_2$-$(1,4,7$-trimethyl-1,4,7-triazacyclononane$)_2$-$(ClO_4)_3$, and mixtures thereof. Others are described in EP-A-0,549,272, which description is incorporated herein by reference. Other ligands suitable for use herein include 1,5,9-trimethyl-1,5,9-triazacyclododecane, 2-methyl-1,4,7-triazacyclononane, 2-methyl-1,4,7-triazacyclononane, 1,2,4,7-tetramethyl-1,4,7-triazacyclononane, and mixtures thereof.

For additional examples of suitable catalysts see U.S. Pat. Nos. 4,246,612 and 5,227,084, which descriptions are incorporated herein by reference. For another example of suitable catalysts, see U.S. Pat. No. 5,194,416, which teaches mononuclear manganese (IV) complexes such as Mn(1,4,7-trimethyl-1,4,7-triazacyclononane)$(OCH_3)_3$ $(PF_6)$, which description is incorporated herein by reference. Still another type of suitably catalyst, as disclosed in U.S. Pat. No. 5,114,606, is a water-soluble complex of manganese (III), and/or (IV) with a ligand which is a non-carboxylate polyhydroxy compound having at least three consecutive C—OH groups, which description is incorporated herein by reference. Other examples include binuclear Mn complexed with tetra-N-dentate and bi-N-dentate ligands, including $N_4Mn^{III}(u-O)_2Mn^{IV}N_4)^+$ and $[Bipy_2Mn^{III}(u-O)_2Mn^{IV}bipy_2]-(ClO_4)_3$.

Further suitable catalysts are described, for example, in EP-A-0,408,131 (cobalt complex catalysts), EP-A-0,384,503, and EP-A-0,306,089 (metallo-porphyrin catalysts), U.S. Pat. No. 4,728,455 (manganese/multidentate ligand catalyst), U.S. Pat. No. 4,711,748 and EP-A-0.224,952, (absorbed manganese on aluminosilicate catalyst), U.S. Pat. No. 4,601,845 (aluminosilicate support with manganese and zinc or magnesium salt), U.S. Pat. No. 4,626,373 (manganese/ligand catalyst), U.S. Pat. No. 4,119,557 (ferric complex catalyst), DE-A-2,054,019 (cobalt chelant catalyst) CA-A-866,191 (transition metal-containing salts), U.S. Pat. No. 4,430,243 (chelants with manganese cations and non-catalytic metal cations), and U.S. Pat. No. 4,728,455 (manganese gluconate catalysts), all of which descriptions are incorporated herein by reference.

3. Thickeners

The stable alkaline hair bleaching compositions of the present invention may include a thickener at a level of from about 0.05% to about 20%, preferably from about 0.1% to about 10%, more preferably from about 0.5% to about 5% by weight. Thickening agents suitable for use in the compositions herein are selected from oleic acid, cetyl alcohol, oleyl alcohol, sodium chloride, cetearyl alcohol, stearyl alcohol, synthetic thickeners such as Carbopol®, Aculyn®& and Salcare® and Elfacos® and mixtures thereof. Preferred thickeners for use herein are Aculyn® 22 steareth-20 methacrylate copolymer, Aculyn® 33 anionic acrylic copolymer, Aculyn® 44 polyurethane resin, and Aculyn® 46 hydrophobically modified nonionic polyol and others, which are available from ISP (International Specialty Products). Also preferred are the Salcare® series of thickeners (SC80, 81, 91, 92, 95, 96 AST) available from Ciba Specialty Chemicals. Also preferred are the series of thickeners available from Akzo Nober such as Elfacos® GT 282S ceteareth-60 myristyl glycol, Elfacos® GT 282 L ceteareth-60 myristyl glycol, Elfacos® T211 PPG 14 Laureth-60 Isophoryl dicarbamate, and Elfacos® T212 PPG-14 Palmeth-60 Hexyl Dicarbamate. Additional thickening agents suitable for use herein include sodium alginate or gum arabic, or cellulose derivatives, such as methyl cellulose or the sodium salt of carboxymethylcellulose or acrylic polymers.

Additional thickeners suitable for use herein are those disclosed in: WO 99/37,047 (nonionic polyurethanes and/or cationic polymers); EP 0,875,237A2 (hydrophobically modified nonionic polyols and polyethoxylated urethane); WO 99/36,047 (polyurethane polymers and/or cationic conditioning agents); WO 98/03,150 (nonionic amphiphilic polymers having at least one fatty chain); and U.S. Pat. No. 5,281,654 (mixture of polyurethanes), all of which descriptions are incorporated herein by reference.

4. Conditioning Agent

The stable alkaline hair bleaching compositions of the present invention may comprise from about 0.01% to about 30%, by weight of the composition, preferably from about 0.1% to about 20%, more preferably from about 0.1% to about 10%, most preferably from about 0.2% to about 6%, of a conditioning agent suitable for application to the hair or skin. It is believed that the conditioning agent provides improved conditioning benefits to the hair, particularly clean hair feel and wet rinse feel.

Suitable conditioning agents for use in the compositions herein are those conditioning agents characterized generally as silicones (e.g. silicone oils, cationic silicones, silicone gums, high refractive silicones, and silicone resins), organic conditioning oils (e.g. hydrocarbon oils, polyolefins, and fatty esters) or combinations thereof, or those conditioning agents which otherwise form liquid, dispersed, particles in the aqueous surfactant matrix herein. Such conditioning agents should be physically and chemically compatible with the essential components of the composition, and should not otherwise unduly impair product stability, aesthetics or performance.

The concentration of the conditioning agent in the hair bleaching composition should be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

a. Silicones

The conditioning agent of the stable alkaline hair bleaching compositions of the present invention is preferably an insoluble silicone conditioning agent. The silicone conditioning agent particles may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair (especially when high refractive index (e.g. above about 1.46) silicone conditioning agents are used (e.g. highly phenylated silicones).

The concentration of the silicone conditioning agent typically ranges from about 0.01% to about 10%, by weight of the composition, preferably from about 0.1% to about 8%, more preferably from about 0.1% to about 5%, most preferably from about 0.2% to about 3%. Non-limiting examples of suitable silicone conditioning agents, and optional suspending agents for the silicone, are described by the Procter & Gamble Company in U.S. Reissue Pat. No. RE 34,584, U.S. Pat. No. 5,104,646, and U.S. Pat. No. 5,106,609, all which are incorporated herein by reference in their entirety. The silicone conditioning agents for use herein preferably have a viscosity, as measured at 25° C., from about 20 to about 2,000,000 centistokes ("csk"), more preferably from about 1,000 to about 1,800,000 csk, even more preferably from about 50,000 to about 1,500,000 csk, most preferably from about 100,000 to about 1,500,000 csk.

The dispersed, silicone conditioning agent particles typically have a number average particle diameter ranging from about 0.01 $\mu$m to about 50 $\mu$m. For small particle application to hair, the number average particle diameters typically range from about 0.01 $\mu$m to about 4 $\mu$m, preferably from about 0.01 $\mu$m to about 2 $\mu$m, more preferably from about 0.01 $\mu$m to about 0.5 $\mu$m. For larger particle application to hair, the number average particle diameters typically range from about 4 $\mu$m to about 50 $\mu$m, preferably from about 6 $\mu$m to about 30 $\mu$m, more preferably from about 9 $\mu$m to about 20 $\mu$m, most preferably from about 12 $\mu$m to about 18 $\mu$m. Conditioning agents having an average particle size of less than about 5 $\mu$m may deposit more efficiently on the hair.

Background material on silicones including sections discussing silicone fluids, gums, and resins, as well as manufacture of silicones, are found in *Encyclopedia of Polymer Science and Engineering*, vol. 15, 2d ed., pages 204–308, John Wiley & Sons, Inc. (1989), which description is incorporated herein by reference.

i. Silicone Oils

Silicone fluids include silicone oils, which are flowable silicone materials having a viscosity, as measured at 25° C., less than 1,000,000 csk, preferably from about 5 csk to about 1,000,000 csk, more preferably from about 10 csk to about 100,000 csk. Suitable silicone oils for use herein include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes which conform to the following general formula (XV):

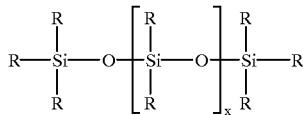

wherein R is aliphatic, preferably alkyl or alkenyl, or aryl, R can be substituted or unsubstituted, and x is an integer from 1 to about 8,000. Suitable unsubstituted R groups for use herein include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure so long as the resulting silicones remain fluid at room temperature, are hydrophobic, are neither irritating, toxic nor otherwise harmful when applied to the hair, are compatible with the other components of the hair bleaching compositions, are chemically stable under normal use and storage conditions, are insoluble in the hair bleaching compositions herein, and are capable of being deposited on and conditioning the hair. The two R groups on the silicon atom of each monomeric silicone unit may represent the same or different groups. Preferably, the two R groups represent the same group.

Preferred alkyl and alkenyl substituents are $C_1$ to $C_5$ alkyls and alkenyls, more preferably from $C_1$ to $C_4$, most preferably from $C_1$ to $C_2$. The aliphatic portions of other alkyl-, alkenyl-, or alkynyl-containing groups (such as alkoxy, alkaryl, and alkamino) can be straight or branched chains, and are preferably from $C_1$ to $C_5$, more preferably from $C_1$ to $C_4$, even more preferably from $C_1$ to $C_3$, most preferably from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length is preferably as described above. The R substituents may also be substituted with other groups, such as halogens (e.g. chloride, fluoride, and bromide), halogenated aliphatic or aryl groups, hydroxy (e.g. hydroxy substituted aliphatic groups), and mixtures thereof. Suitable halogenated R groups could include, for example, tri-halogenated (preferably tri-fluoro) alkyl groups such as $—R^1CF_3$, wherein $R^1$ is a $C_1$–$C_3$ alkyl. An example of such a polysiloxane includes, but is not limited to, polymethyl 3,3,3-trifluoropropylsiloxane.

Suitable R groups for use herein include, but are not limited to: methyl, ethyl, propyl, phenyl, methylphenyl and phenylmethyl. Specific non-limiting examples of preferred silicones include: polydimethyl siloxane, polydiethylsiloxane, and polymethylphenylsiloxane. Polydimethylsiloxane is especially preferred. Other suitable R groups include: methyl, methoxy, ethoxy, propoxy, and aryloxy. The three R groups on the end caps of the silicone may represent the same or different groups.

Non-volatile polyalkylsiloxane fluids that may be used include, for example, low molecular weight polydimethylsiloxanes. These siloxanes are available, for example, from the General Electric Company in their Viscasil R and SF 96 series, and from Dow Corning in their Dow Corning 200 series. Polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid. Polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide concentrations must be sufficiently low to prevent solubility in water and the composition described herein.

Alkylamino substituted silicones suitable for use herein include, but are not limited to, those which conform to the following general formula (XVI):

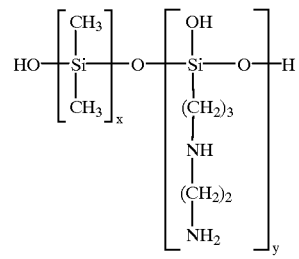

wherein x and y are integers. This polymer is also known as "amodimethicone."

ii. Cationic Silicones

Cationic silicone fluids suitable for use herein include, but are not limited to, those which conform to the general formula (XVII):

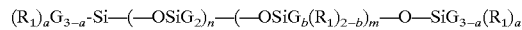

wherein G is hydrogen, phenyl, hydroxy, or $C_1$–$C_8$ alkyl, preferably methyl; a is 0 or an integer having a value from 1 to 3, preferably 0; b is 0 or 1, preferably 1; n is a number from 0 to 1,999 preferably from 49 to 149; m is an integer from 1 to 2,000, preferably from 1 to 10; the sum of n and m is a number from 1 to 2,000, preferably from 50 to 150; $R_1$ is a monovalent radical conforming to the general formula $CqH_{2q}L$, wherein q is an integer having a value from 2 to 8 and L is selected from the following groups:

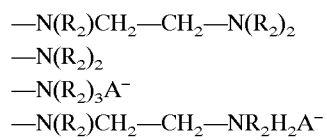

wherein $R_2$ is hydrogen, phenyl, benzyl, or a saturated hydrocarbon radical, preferably an alkyl radical from about $C_1$ to about $C_{20}$, and $A^-$ is a halide ion.

An especially preferred cationic silicone corresponding to formula (XVII) is the polymer known as "trimethylsilylamodimethicone", which is shown below in formula (XVIII):

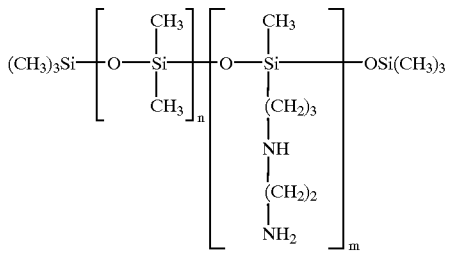

Other silicone cationic polymers which may be used herein are represented by the general formula (XIX):

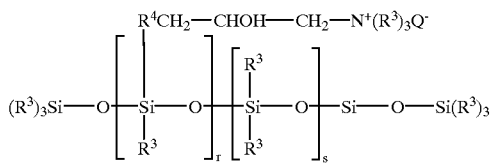

wherein $R^3$ is a monovalent hydrocarbon radical from $C_1$ to $C_{18}$, preferably an alkyl or alkenyl radical, such as methyl; $R_4$ is a hydrocarbon radical, preferably a $C_1$ to $C_{18}$ alkylene radical or a $C_{10}$ to $C_{18}$ alkyleneoxy radical, more preferably a $C_1$ to $C_8$ alkyleneoxy radical; $Q^-$ is a halide ion, preferably chloride; r is an average statistical value from 2 to 20, preferably from 2 to 8; s is an average statistical value from 20 to 200, preferably from 20 to 50. A preferred polymer of this class is known as UCARE SILICONE ALE 56™, available from Union Carbide.

iii. Silicone Gums

Other silicone fluids suitable for use herein are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, *Chemistry and Technology of Silicones*, New York: Academic Press (1968); and in General Electric Silicone Rubber Product Data Sheets SE 30, SE 33, SE 54 and SE 76, all of which descriptions are incorporated herein by reference. The silicone gums will typically have a weight average molecular weight in excess of about 200,000, preferably from about 200,000 to about 1,000,000. Specific non-limiting examples of silicone gums for use herein include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

iv. High Refractive Index Silicones

Other non-volatile, insoluble silicone fluid conditioning agents that are suitable for use herein are those known as "high refractive index silicones," having a refractive index of at least about 1.46, preferably at least about 1.48, more preferably at least about 1.52, most preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (XV) above, as well as cyclic polysiloxanes such as those represented by Formula (XX) below:

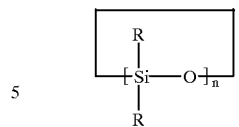

wherein R is as defined above, and n is a number from about 3 to about 7, preferably from about 3 to about 5.

The high refractive index polysiloxane fluids contain an amount of aryl-containing R substituents sufficient to increase the refractive index to the desired level, which is described above. Additionally, R and n must be selected so that the material is non-volatile.

Aryl-containing substituents include those which contain alicyclic and heterocyclic five and six member aryl rings and those which contain fused five or six member rings. The aryl rings themselves can be substituted or unsubstituted. Substituents include aliphatic substituents, and may also include alkoxy substituents, acyl substituents, ketones, halogens (e.g., Cl and Br), amines, and the like. Examples of aryl-containing groups include, but are not limited to, substituted and unsubstituted arenes, such as phenyl, and phenyl derivatives, such as phenyls with $C_1$–$C_5$ alkyl or alkenyl substituents. Specific non-limiting examples include: allylphenyl, methyl phenyl and ethyl phenyl, vinyl phenyls (e.g. styrenyl), and phenyl alkynes (e.g. phenyl $C_2$–$C_4$ alkynes). Heterocyclic aryl groups include, but are not limited to, substituents derived from furan, imidazole, pyrrole, pyridine, and the like. Examples of fused aryl ring substituents include, but are not limited to, napthalene, coumarin, and purine.

Generally, the high refractive index polysiloxane fluids will have a degree of aryl-containing substituents of at least about 15%, preferably at least about 20%, more preferably at least about 25%, even more preferably at least about 35%, most preferably at least about 50%. Typically, the degree of aryl substitution will be less than about 90%, more generally less than about 85%, preferably from about 55% to about 80%.

The high refractive index polysiloxane fluids are also characterized by relatively high surface tensions as a result of their aryl substitution. Generally, the polysiloxane fluids will have a surface tension of at least about 24 dynes/cm², typically at least about 27 dynes/cm². Surface tension, for purposes hereof, is measured by a de Nouy ring tensiometer according to Dow Corning Corporate Test Method CTM 0461 (Nov. 23, 1971). Changes in surface tension can be measured according to the above test method or according to ASTM Method D 1331.

Preferred high refractive index polysiloxane fluids have a combination of phenyl or phenyl derivative substituents (most preferably phenyl), with alkyl substituents, preferably $C_1$–$C_4$ alkyl (most preferably methyl), hydroxy, or $C_1$–$C_4$ alkylamino (especially —$R^1NHR^2NH_2$ wherein each $R^1$ and $R^2$ independently is a $C_1$–$C_3$ alkyl, alkenyl, and/or alkoxy). High refractive index polysiloxanes are available from Dow Corning, Huls America, and General Electric.

When high refractive index silicones are used herein, they are preferably used in solution with a spreading agent, such as a silicone resin or a surfactant, to reduce the surface tension by a sufficient amount to enhance spreading and thereby enhance the glossiness (subsequent to drying) of hair treated with the compositions. Generally, an amount of the spreading agent is used that is sufficient to reduce the surface tension of the high refractive index polysiloxane fluid by at least about 5%, preferably at least about 10%, more preferably at least about 15%, even more preferably at least about 20%, most preferably at least about 25%. Reductions in surface tension of the polysiloxane fluid/spreading agent mixture may improve shine of the hair.

Also, the spreading agent will preferably reduce the surface tension by at least about 2 dynes/cm$^2$, preferably at least about 3 dynes/cm$^2$, even more preferably at least about 4 dynes/cm$^2$, most preferably at least about 5 dynes/cm$^2$.

The surface tension of the mixture of the polysiloxane fluid and the spreading agent, at the proportions present in the final product, is preferably less than or equal to about 30 dynes/cm$^2$, more preferably less than or equal to about 28 dynes/cm$^2$, most preferably less than or equal to about 25 dynes/cm$^2$. Typically, the surface tension will be in the range from about 15 dynes/cm$^2$ to about 30 dynes/cm$^2$, more typically from about 18 dynes/cm$^2$ to about 28 dynes/cm$^2$, and most generally from about 20 dynes/cm$^2$ to about 25 dynes/cm$^2$.

The weight ratio of the highly arylated polysiloxane fluid to the spreading agent will, in general, be from about 1000:1 to about 1:1, preferably from about 100:1 to about 2:1, more preferably from about 50:1 to about 2:1, most preferably from about 25:1 to about 2:1. When fluorinated surfactants are used, particularly high polysiloxane fluid to spreading agent ratios may be effective due to the efficiency of these surfactants. Thus, it is contemplated that ratios significantly above 1000:1 may be used.

Silicone fluids suitable for use herein are disclosed in U.S. Pat. No. 2,826,551, U.S. Pat. No. 3,964,500, U.S. Pat. No. 4,364,837, British Pat. No. 849,433, and *Silicon Compounds*, Petrarch Systems, Inc. (1984), all of which descriptions are incorporated herein by reference.

v. Silicone Resins

Silicone resins may be included in the silicone conditioning agent of the compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin. As is apparent to one of ordinary skill in the art, the degree of cross-linking that is required in order to result in a silicone resin will vary according to the specific silane units incorporated into the silicone resin. Generally, silicone materials which have a sufficient level of trifunctional and tetrafunctional siloxane monomer units (and hence, a sufficient level of cross-linking) such that they dry down to a rigid, or hard, film are considered to be silicone resins. The ratio of oxygen atoms to silicon atoms is indicative of the level of cross-linking in a particular silicone material. Silicone resins suitable for use in the compositions of the present invention generally have at least about 1.1 oxygen atoms per silicon atom. Preferably, the ratio of oxygen to silicon atoms is at least about 1.2:1.0. Silanes used in the manufacture of silicone resins include, but are not limited to: monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are available from General Electric as GE SS4230 and GE SS4267. Commercially available silicone resins are generally supplied in a dissolved form in a low viscosity volatile or non-volatile silicone fluid. The silicone resins for use herein should be supplied and incorporated into the present compositions in such dissolved form, as will be readily apparent to one of ordinary skill in the art. Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetrafunctional unit $SiO_2$. Primes of the unit symbols (e.g. M', D', T', and Q') denote substituents other than methyl, and must be specifically defined for each occurrence. Typical alternate substituents include, but are not limited to, groups such as vinyl, phenyls, amines, hydroxyls, and the like. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin indicates higher levels of cross-linking. As discussed above, however, the overall level of cross-linking can also be indicated by the oxygen to silicon ratio.

Preferred silicone resins for use in the compositions of the present invention include, but are not limited to MQ, MT, MTQ, MDT and MDTQ resins. Methyl is a preferred silicone substituent. Especially preferred silicone resins are MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, is preferably from about 4:1 to about 400:1, more preferably from about 9:1 to about 200:1, most preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

b. Organic Conditioning Oils

The conditioning component of the compositions of the present invention may also comprise from about 0.05% to about 3%, by weight of the composition, preferably from about 0.08% to about 1.5%, more preferably from about 0.1% to about 1%, of at least one organic conditioning oil as the conditioning agent, either alone or in combination with other conditioning agents, such as the silicones (described above). The conditioning oils may add shine and luster to the hair. Additionally, they may enhance dry combing and dry hair feel.

The organic conditioning oils suitable for use as the conditioning agent herein are preferably low viscosity, water insoluble, liquids selected from the hydrocarbon oils, polyolefins, fatty esters, and mixtures thereof. The viscosity, as measured at 40° C., of such organic conditioning oils is preferably from about 1 centipoise to about 200 centipoise, more preferably from about 1 centipoise to about 100 centipoise, most preferably from about 2 centipoise to about 50 centipoise.

i. Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2,2,4,4,6,6,8,8-dimethyl-10-methylundecane and 2,2,4,4,6,6-dimethyl-8-methylnonane, available from Permethyl Corporation. Hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation, another is Versagel® ME 750 hydrogenated polyisobutene, available from Penreco.

ii. Polyolefins

Organic conditioning oils for use in the compositions of the present invention can also include liquid polyolefins, more preferably liquid poly-α-olefins, most preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents. Preferred hydrogenated α-olefin monomers include, but are not limited to: 1-hexene to 1-hexadecenes, 1-octene to 1-tetradecene, and mixtures thereof.

iii. Fatty Esters

Other suitable organic conditioning oils for use as the conditioning agent in the compositions of the present invention include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Suitable for use in the compositions of the present invention are alkyl and alkenyl esters of fatty acids having from about $C_{10}$ to about $C_{22}$ aliphatic chains, and alkyl and alkenyl fatty alcohol carboxylic acid esters having a $C_{10}$ to about $C_{22}$ alkyl and/or alkenyl alcohol-derived aliphatic chain, and mixtures thereof. Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are mono-carboxylic acid esters of the general formula R'COOR, wherein R' and R are alkyl or alkenyl radicals, and the sum of carbon atoms in R' and R is at least 10, preferably at least 20. The mono-carboxylic acid ester need not necessarily contain at least one chain with at least 10 carbon atoms; rather the total number of aliphatic chain carbon atoms must be least 10. Specific non-limiting examples of mono-carboxylic acid esters include: isopropyl myristate, glycol stearate, and isopropyl laurate.

Still other fatty esters suitable for use in the compositions of the present invention are di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, adipic acid, hexanoic acid, heptanoic acid, and octanoic acid). Specific non-limiting examples of di- and tri-alkyl and alkenyl esters of carboxylic acids include isocetyl stearyol stearate, diisopropyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the compositions of the present invention are glycerides, including, but not limited to, mono-, di-, and tri-glycerides, preferably di- and tri-glycerides, most preferably triglycerides. For use in the compositions described herein, the glycerides are preferably the mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the compositions of the present invention are water insoluble synthetic fatty esters. Some preferred synthetic esters conform to the general formula (XXI):

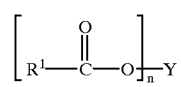

wherein $R^1$ is a $C_7$ to $C_9$ alkyl, alkenyl, hydroxyalkyl or hydroxyalkenyl group, preferably a saturated alkyl group, more preferably a saturated, linear, alkyl group; n is a positive integer having a value from 2 to 4, preferably 3; and Y is an alkyl, alkenyl, hydroxy or carboxy substituted alkyl or alkenyl, having from about 2 to about 20 carbon atoms, preferably from about 3 to about 14 carbon atoms. Other preferred synthetic esters conform to the general formula (XXII):

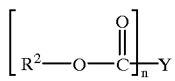

wherein $R^2$ is a $C_8$ to $C_{10}$ alkyl, alkenyl, hydroxyalkyl or hydroxyalkenyl group; preferably a saturated alkyl group, more preferably a saturated, linear, alkyl group; n and Y are as defined above in formula (XXII).

Specific non-limiting examples of suitable synthetic fatty esters for use in the compositions of the present invention include: P-43 ($C_8$–$C_{10}$ triester of trimethylolpropane), MCP-684 (tetraester of 3,3 diethanol-1,5 pentadiol), MCP 121 ($C_8$–$C_{10}$ diester of adipic acid), all of which are available from Mobil Chemical Company.

c. Other Conditioning Agents

Also suitable for use in the compositions herein are the conditioning agents described by the Procter & Gamble Company in U.S. Pat. Nos. 5,674,478, and 5,750,122, both of which are incorporated herein in their entirety by reference. Yet other conditioning agents suitable for use herein are the series of conditioners available from International Specialty Chemicals, such as the Gafquat® series of quaternary copolymers, and the Arquad® series of quaternary ammonium salts, available from Akzo Nobel. Also suitable for use herein are those conditioning agents described in U.S. Pat. No. 4,529,586 (Clairol), U.S. Pat. No. 4,507,280 (Clairol), U.S. Pat. No. 4,663,158 (Clairol), U.S. Pat. No. 4,197,865 (L'Oreal), U.S. Pat. No. 4,217,914 (L'Oreal), U.S. Pat. No. 4,381,919 (L'Oreal), and U.S. Pat. No. 4,422,853 (L'Oreal), all of which descriptions are incorporated herein by reference.

Some other preferred silicone conditioning agents for use in the stable alkaline hair bleaching compositions of the present invention include: Abil® S 201 (dimethicone/sodium PG-propyldimethicone thiosulfate copolymer), available from Goldschmidt; DC Q2-8220 (trimethylsilyl amodimethicone) available from Dow Corning; DC 949 (amodimethicone, cetrimonium chloride, and Trideceth-12), available from Dow Corning; DC 749 (cyclomethicone and trimethylsiloxysilicate), available from Dow Corning; DC2502 (cetyl dimethicone), available from Dow Corning; BC97/004 and BC 99/088 (amino functionalized silicone microemulsions), available from Basildon Chemicals; GE SME253 and SM2115-D2_and SM2658 and SF1708 (amino functionalized silicone microemulsions), available from General Electric; siliconized meadowfoam seed oil, available from Croda; and those silicone conditioning agents described by GAF Corp. in U.S. Pat. No. 4,834,767 (quaternized amino lactam), by Biosil Technologies in U.S. Pat. No. 5,854,319 (reactive silicone emulsions containing amino acids), and by Dow Corning in U.S. Pat. No. 4,898,585 (polysiloxanes), all of which descriptions are incorporated herein by reference.

Other preferred conditioning agents for use herein include quaternary species, such as Quadrisoft™ LM 200 (quaternized cellulose), available from Amerchol; Polymer KG30M (polyquaternium 10 and quaternized cellulose), Incroquat® behenyl trimonium methosulfate (cetearyl alcohol and behentrimonium methosulfate), available from Croda; Merquat® 5 (quaternary ammonium resin), available from Calgon; Gafquat® series 755 and 440 (cationic quaternized copolymers), available from ISP; Akypoquat® 131, available from Kao; Salcare® SC 60 (quaternary ammonium resin), or Salcare® SC95 or SC96 (cationic liquid dispersion thickeners), all available from Ciba; and Meadowquat® HG (PEG-2-dimeadowfoamamidoethylmonium methosulfate), available from Fanning.

Still yet other preferred conditioning agents for use herein include protein derivatives, such as Crodasone® W (hydrolyzed wheat protein silicone copolymer) and Hydrotriticum® QM (quaternary hydrolyzed wheat protein), both available from Croda; and polymers, such as Polyox® 60K and Polyox® 10 (polyoxyethylenes), both available from Amerchol, and polyethyleneimines, available from BASF.

d. Cationic Polymer

The stable alkaline hair bleaching compositions of the present invention may comprise from about 0.02% to about 5%, by weight of the composition, preferably from about 0.05% to about 3%, more preferably from about 0.1% to about 2%, most preferably from about 0.5% to about 1%, of at least one organic, cationic deposition and conditioning polymer suitable for application to the hair or skin. Such cationic polymers should be physically and chemically compatible with the essential components described herein, and should not otherwise unduly impair product stability, aesthetics or performance.

i. Physical Properties and Types of the Cationic Polymers

The cationic polymers useful in the present invention must be selected and must be present at a level such that the cationic polymers are soluble in the hair bleaching composition. The average molecular weight of cationic conditioning polymers suitable for use herein is typically from about 5,000 to about 10,000,000, preferably from about 100,000 to about 2,000,000, more preferably from about 200,000 to about 1,500,000, more preferably from about 250,000 to about 850,000, more preferably from about 350,000 to about 850,000, most preferably from about 350,000 to about 500,000. The polymers have a cationic charge density typically from about 0.2 meq/g to about 7 meq/g, as measured at the pH of intended use of the hair bleaching composition, preferably from about 0.4 meq/gm to about 5 meq/g, more preferably from about 0.6 meq/g to about 2 meq/g, more preferably from about 0.5 meq/g to about 0.1 meq/g, more preferably from about 0.5 meq/g to about 0.9 meq/g. Any anionic counterions may be use in association with the cationic polymers so long as the cationic polymers remain soluble in the composition, and so long as the counterions are physically and chemically compatible with the essential components of the hair bleaching composition or do not otherwise unduly impair product performance, stability or aesthetics. Non-limiting examples of such counterions include: halides (e.g., chloride, fluoride, bromide, iodide), sulfate, methylsulfate, and mixtures thereof. Examples of cationic polymers which may be suitably employed in the hair bleaching compositions herein include, but are not limited to cationic polysaccharides (e.g. cationic cellulose derivatives and cationic guars), copolymers of vinyl monomers, vinyl pyrrolidone copolymers, cationic modified proteins, and certain polymeric quaternary salts. Such cationic polymers are described in detail below.

ii. Cationic Polysaccharides

Preferred cationic polymers for use in the stable alkaline hair bleaching compositions of the present invention are those known as cationic polysaccharides. Cationic polysaccharides are those polymers based on $C_5$ to $C_6$ sugars and derivatives which have been made cationic by engrafting of cationic moieties on the polysaccharide backbone, and include homopolymers, copolymers, terpolymers, and so forth, of quaternary ammonium or cationic amine-substituted monomer units, optionally in combination with non-cationic monomers. The polysaccharides may be composed of one type of sugar or of more than one type. The cationic amines can be primary, secondary, or tertiary amines (preferably secondary or tertiary), depending upon the particular species and the selected pH of the hair bleaching composition. The monomers may be in straight chain or branched chain geometric arrangements. All of the monomer units may have cationic nitrogen-containing moieties attached thereto, preferably some of the monomer units do not have such moieties attached. Non-limiting examples of cationic polysaccharides are described in the *CTFA Cosmetic Ingredient Dictionary*, 3d ed., edited by Estrin, Crosley, and Haynes, (The Cosmetic, Toiletry, and Fragrance Association, Inc., Washington, D.C. (1982), which description is incorporated herein by reference.

Cationic polysaccharide polymers include the following: cationic celluloses and hydroxyethylcelluloses; cationic starches and hydroxyalkyl starches; cationic polymers based on the galactomannan copolymer known as guar gum obtained from the endosperm of the guar bean; cationic polymers based on arabinose vegetable gums; cationic polymers derived from xylose polymers (such as those found in wood, straw, cottonseed hulls, and corn cobs); cationic polymers derived from fucose polymers (such as those found as a component of cell walls in seaweed); cationic polymers derived from fructose polymers (such as Inulin, which is found in certain plants); cationic polymers based on acid-containing sugars (such as galacturonic acid and glucouronic acid); cationic polymers based on amine sugars (such as galactosamine and glucosamine); cationic polymers based on 5 and 6 member ring polyalcohols; cationic polymers based on galactose monomers (such as those found in plant gums and mucilates); and cationic polymers based on mannose monomers (such as those found in plants, yeasts, and red algae). Preferred are cationic celluloses and hydroxyethylcelluloses; cationic starches and hydroxyalkyl starches; cationic polymers based on guar gum, and mixtures thereof.

1). Cationic Cellulose Derivatives

Suitable polysaccharide cationic polymers for use in the stable alkaline hair bleaching compositions of the present invention are the cationic cellulose derivatives and cationic starch derivatives. Such cationic polymers include those which conform to the general Formula (XXIII):

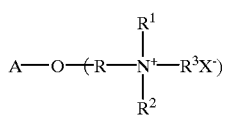

wherein A is an anhydroglucose residual group (e.g. a starch or cellulose anhydroglucose residual); R is an alkylene oxyalkylene, polyoxyalkylene, or hydroxyalkylene group, or combination thereof; $R^1$, $R^2$, and $R^3$ are independently alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$, and $R^3$) preferably being about 20 or less; and X is an anionic counterion as described above. Preferred cationic cellulose polymers include, but are not limited to, those polymers available from Amerchol Corporation, in their Polymer JR and LR series of polymers, as salts of hydroxyethyl cellulose reacted with trimethyl ammonium substituted epoxide, known in the industry (CTFA) as Polyquaternium 10 (e.g. JR 30M®, available from Amerchol Corporation). Preferred Polyquaternium 10 polymers for use herein, typically have a charge density from about 0.3 meq/g to about 3 meq/g and a molecular weight from about 200,000 to about 1,500,00. Another non-limiting of a preferred type of cationic cellulose includes the polymeric quaternary ammonium salt of hydroxyethyl cellulose reacted with lauryl dimethyl ammonium-substituted epoxide, known in the industry (CTFA) as Polyquaternium 24, (e.g. Polymer LM 200®, available from Amerchol Corporation).

Also suitable for use herein are those quaternary nitrogen-containing cellulose copolymers of hydroxyethylcellulose reacted with diallyldimethyl ammonium chloride, known in the industry (CTFA) as Polyquaternium 4 (e.g. Celquat® H-100, available from National Starch Corporation). Quaternary nitrogen-containing cellulose ethers suitable for use herein are described by the Procter & Gamble Company in U.S. Pat. No. 3,962,418, which is incorporated herein by reference in its entirety, and still other copolymers of etherified cellulose and starch suitable for use herein are described in by L'Oreal in U.S. Pat. No. 3,958,581, which description is incorporated herein by reference.

2). Cationic Guars

Other suitable polysaccharide cationic polymers for use in the stable alkaline hair bleaching compositions of the present invention are cationic guar polymers. Guars are cationically substituted galactomannan (guar) gum derivatives. The molecular weight of such derivatives ranges typically from about 50,000 to about 2,500,000, preferably from about 50,000 to about 1,000,000, more preferably from about 50,000 to about 700,000.

Guar gum for use in preparing these guar gum derivatives is typically obtained as a naturally occurring material from the seeds of the guar plant. The guar molecule itself is a straight chain mannan branched at regular intervals with single membered galactose units on alternative mannose units. The mannose units are linked to each other by means of β (1–4) glycosidic linkages. The galactose branching arises by way of an (1–6) linkage. Cationic derivatives of the guar gums are obtained by reaction between the hydroxyl groups of the polygalactomannan and reactive quaternary ammonium compounds. The degree of substitution of the cationic groups onto the guar structure must be sufficient to provide the requisite cationic charge density described above.

Suitable quaternary ammonium compounds for use in forming the cationic guar polymers include those conforming to the general formula (XXIV):

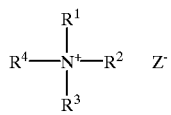

wherein where $R^1$, $R^2$ and $R^3$ are methyl or ethyl groups; $R^4$ is either an epoxyalkyl group of the general formula (XXV):

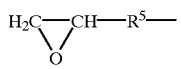

or $R^4$ is a halohydrin group of the general Formula (XXVI):

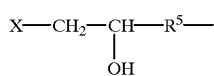

wherein $R^5$ is a $C_1$ to $C_3$ alkylene; X is chlorine or bromine, and Z is an anion such as $Cl^-$, $Br^-$, $I^-$ or $HSO_4^-$.

Cationic guar polymers (cationic derivatives of guar gum) formed from the reagents described above are represented by the general Formula (XXVII):

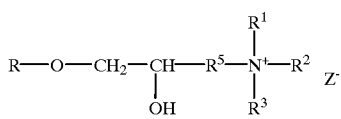

wherein R is guar gum. Preferably, the cationic guar polymer is guar hydroxypropyltrimethylammonium chloride, which can be more specifically represented by the general Formula (XXVIII):

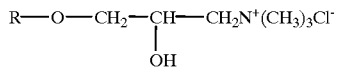

Specific non-limiting examples of cationic guar polymers which conform to Formula XXVIII include: Jaguar® C 13S, having a cationic charge density of 0.8 meq/g (available from Rhodia Company) and Jaguar® C 17, having a cationic charge density of 1.6 meq/g (available from Rhodia Company). Other suitable cationic guar polymers include hydroxypropylated cationic guar derivatives. Still other suitable cationic polymers include copolymers of etherified guar, some examples of which are described in U.S. Pat. No. 3,958,581, which description is incorporated herein by reference.

iii. Copolymers of Vinyl Monomers

Other suitable cationic polymers for use in the stable alkaline hair bleaching compositions of the present invention are copolymers of vinyl monomers, having cationic protonated amine or quaternary ammonium functionalities, reacted with water soluble monomers. Non-limiting examples of such monomers include: acrylamide, methacrylamide, alkyl and dialkyl acrylamides, alkyl and dialkyl methacrylamides, alkyl acrylate, alkyl methacrylate, vinyl caprolactone, vinyl pyrrolidone, and mixtures thereof. The alkyl and dialkyl substituted monomers preferably have from $C_1$ to $C_7$ alkyl groups, more preferably from $C_1$ to $C_3$ alkyl groups. Other suitable monomers include vinyl esters, vinyl alcohol (made by hydrolysis of polyvinyl acetate), maleic anhydride, propylene glycol, ethylene glycol, and mixtures thereof.

Suitable cationic protonated amino and quaternary ammonium monomers, for inclusion in the cationic polymers of the hair bleaching composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts; and vinyl quaternary ammonium monomers having cyclic cationic nitrogen-containing rings such as pyridinium, imidazolium, and quaternized pyrrolidones, such as alkyl vinyl imidazolium, alkyl vinyl pyridinium, and alkyl vinyl pyrrolidone salts. The alkyl portions of these monomers are preferably lower alkyls such as the $C_1$–$C_3$ alkyls.

Suitable amine-substituted vinyl monomers for use herein include, dialkylaminoalkyl acrylamide, and dialkylaminoalkyl methacrylamide, wherein the alkyl groups are preferably $C_1$ to $C_7$ hydrocarbyls, more preferably $C_1$ to $C_3$ alkyls.

iv. Vinyl Pyrrolidone Copolymers

Other suitable cationic polymers for use in the stable alkaline hair bleaching compositions of the present invention include: copolymers of 1-vinyl-2-pyrrolidone and 1-vinyl-3-methylimidazolium salt (e.g., chloride salt), known in the industry (CTFA) as Polyquaternium 16 (e.g. Luviquat® FC 370, available from BASF Wyandotte Corporation); copolymers of 1-vinyl-2-pyrrolidone and dimethylaminoethyl methacrylate, known in the industry (CTFA) as Polyquaternium 11 (e.g. Gafquat® 755N, available from ISP Corporation); cationic diallyl quaternary ammonium-containing polymers, including, for example, dimethyldiallyl-ammonium chloride homopolymer, known in the industry (CTFA) as Polyquaternium 6; copolymers of acrylamide and dimethyldiallylammonium chloride, known in the industry (CTFA) as Polyquaternium 7; and mineral acid salts of amino-alkyl esters of homopolymers and copolymers of unsaturated $C_3$ to $C_5$ carboxylic acids, such as those described in U.S. Pat. No. 4,009,256, which description is incorporated herein by reference.

v. Cationic Modified Proteins and Polymeric Quaternary Salts

Still other cationic polymers for use in the stable alkaline hair bleaching compositions of the present invention are cationic modified proteins, such as lauryldimonium hydroxypropyl collagen (e.g. Croquat® L, available from Croda Corporation), or cocodimonium hydroxypropyl hydrolized hair keratin (e.g. Croquat® HH, available from Croda Corporation). Other cationic polymers include the polymeric quaternary salt prepared the reaction of adipic acid and dimethylaminopropylamine, reacted with dichloroethyl ether, known in the industry (CTFA) as Polyquaternium 2 (e.g. Mirapol® AD-1, available from Rhodia), and the polymeric quaternary salt prepared by the reaction of azelaic acid and dimethylaminopropylether, known in the industry (CTFA) as Polyquaternium 18 (e.g. Mirapol(g AZ-1, available from Rhodia Corporation).

e. Polyalkylene Glycol

The stable alkaline hair bleaching compositions of the present invention may comprise from about 0.005% to about 1.5%, by weight of the composition preferably from about 0.025% to about 0.1%, more preferably from about 0.05% to about 1%, more preferably from about 0.1% to about 0.5%, most preferably from about 0.1% to about 0.3%, of selected polyalkylene glycols suitable for application to the hair or skin. Such polyalkylene glycols should be physically and chemically compatible with the essential components described herein, and should not otherwise unduly impair product stability, aesthetics, or performance.

The polyalkylene glycols suitable for use in the hair bleaching compositions herein are characterized by the general Formula (XXIX):

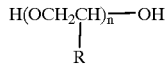

wherein R is hydrogen, methyl, or mixtures thereof, preferably hydrogen, and n is an integer having an average value from about 1,500 to about 120,000, preferably from about 1,500 to about 50,000, more preferably from about 2,500 to about 25,000, and most preferably from about 3,500 to about 15,000. When R is hydrogen, these materials are polymers of ethylene oxide, which are also known as polyethylene glycols. When R is methyl, these materials are polymers of propylene oxide, which are also known as polypropylene glycols. When R is methyl, it is also understood that various positional isomers of the resulting polymers can exist. Preferred for use herein are polyethylene glycols, polypropylene glycols, and mixtures thereof.

Specific non-limiting examples of polyethylene glycol polymers for use in the stable alkaline hair bleaching compositions of the present invention include: PEG 2M, wherein R is hydrogen and n has an average value of about 2,000 (e.g. Polyox WSR® N-10, available from Union Carbide); PEG 5M, wherein R is hydrogen and n has an average value of about 5,000 (e.g. Polyox WSR® N-35 and Polyox WSR® N-80, both available from Union Carbide); PEG 7M, wherein R is hydrogen and n has an average value of about 7,000 (e.g. Polyox WSR® N-750, available from Union Carbide); PEG 9M, wherein R is hydrogen and n has an average value of about 9,000 (e.g. Polyox WSR® N-3333, available from Union Carbide); PEG 14 M, wherein R is hydrogen and n has an average value of about 14,000 (e.g. Polyox WSR® N-3000, available from Union Carbide); PEG 23M, wherein R is hydrogen and n has an average value of about 23,000 (e.g. Polyox WSR® N-12k, available from Union Carbide); PEG 90M, wherein R is hydrogen and n has an average value of about 90,000 (e.g. Polyox WSR® 301, available from Union Carbide); and PEG 100M, wherein R is hydrogen and n has an average value of about 100,000 (e.g. Carbowax PEG 4600™, available from Union Carbide). Preferred polyethylene glycols include PEG 7M, PEG 14M, PEG 25M, PEG 90M, and mixtures thereof.

II. Optional Components

The stable alkaline hair bleaching compositions of the present invention may, in some embodiments, further comprise additional optional components known or otherwise effective for use in hair care or personal care products. Hair coloring agents, diluents, enzymes, anti-oxidants and other optional components are described in detail below. Any optional component(s) should be physically and chemically compatible with the essential components of the composition, and should not otherwise unduly impair product stability, aesthetics or performance.

A. Hair Coloring Agents

The stable alkaline hair bleaching compositions of the present invention may, in some embodiments, further comprise from about 0.001% to about 5%, by weight, of an oxidative or non-oxidative hair coloring agent. Such hair coloring agents may be used in combination with the essential components to formulate permanent, demi-permanent, semi-permanent or temporary hair dye compositions.

Permanent hair dye compositions as defined herein are compositions which once applied to the hair are substantially resistant to wash-out. Demi-permanent hair dye compositions as defined herein are compositions which are substantially removed from the hair after up to 24 washes. Semi-permanent hair dye compositions as defined herein are compositions which once applied to the hair are substantially removed from the hair after up to 10 washes. Temporary hair dye compositions as defined herein are compositions which once applied to the hair are substantially removed from the hair after up to 2 washes. These different types of hair coloring compositions can be formulated via the specific combination of oxidant and/or dyes at different levels and ratios. Wash out as defined herein is the process by which hair color is removed from the hair over time during normal hair cleansing regimen. Washfastness as defined herein, means, the resistance of the dyed hair to wash out.

1. Oxidative Hair Coloring Agents

A preferred hair coloring agent herein is an oxidative hair coloring agent. The concentration of each oxidative hair coloring agent in the coloring compositions according to the present invention is preferably from about 0.001% to about 3% by weight of the composition, more preferably from about 0.01% to about 2%.

The total combined level of oxidative hair coloring agents in the compositions according to the present invention is from about 0.001% to about 5%, by weight of the composition, preferably from about 0.01% to about 4%, more preferably from about 0.1% to about 3%, and yet more preferably from about 0.1% to about 1%.

Any oxidative hair coloring agent can be used in the compositions according to the present invention. Typically, but without intending to be limited thereby, oxidative hair coloring agents, comprise at least two components which are collectively referred to as dye forming intermediates. Primary intermediates are commonly known as "precursors" and secondary intermediates are commonly known as "couplers." Dye forming intermediates can react in the presence of a suitable oxidant to form a colored molecule.

The dye forming intermediates used in oxidative hair colorants include: aromatic diamines, aminophenols, various heterocycles, phenols, napthols and their various derivatives. These dye forming intermediates can be broadly classified as; primary intermediates and secondary intermediates. Primary intermediates (precursors) are chemical compounds which become activated upon oxidation and can then react with each other and/or with secondary intermediates (couplers) to form colored dye complexes. The secondary intermediates (couplers) are generally colorless molecules which can form colors in the presence of activated primary intermediates (precursors) and are used with other intermediates to generate specific color effects or to stabilize the color.

While not being bound by any particular theory it is proposed herein that the process by which color is generated from these primary intermediates and secondary coupler compounds generally includes a stepwise sequence whereby the primary intermediate can become activated (by oxidation), and then enjoins with a coupler to give a dimeric, conjugated colored species, which in turn can enjoin with another 'activated' primary intermediate to produce a trimeric conjugated colored molecule. By way of illustration, such a reaction sequence might look like the one set forth below, wherein the primary dye intermediate (A) is generally understood to be 'activated' (oxidized) by active species (OX) liberated during the decomposition of the preformed organic peroxyacid oxidizing agent and/or any additional optional oxidizing agents, if present. The 'activated' dye intermediate, which may have structure (B), can then react with a suitable coupler to form a larger 'colored' dye compounds such as dimer and trimers.

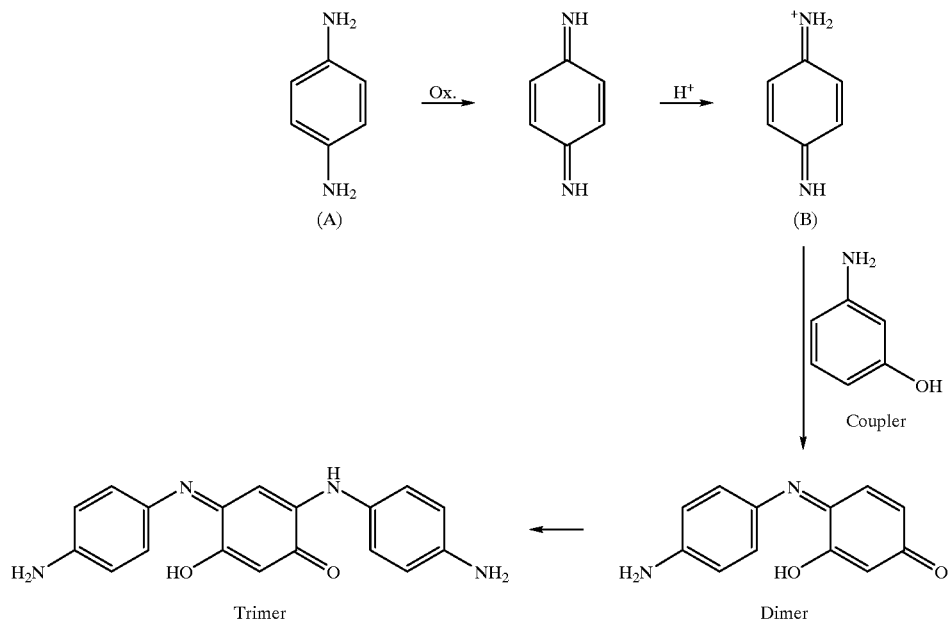

Oxidative dye intermediates diffuse into the hair shaft, which may have been pre-swollen by action of an hair swelling agent, if present, and then are activated and coupled to form larger dye complexes within the hair shaft which are less readily washed out.

a. Oxidative Primary Intermediates (precursors)

Generally, oxidative dye primary intermediates include those monomeric materials which, on oxidation, form oligomers or polymers having extended conjugated systems of electrons in their molecular structure. Because of the new electronic structure, the resultant oligomers and polymers exhibit a shift in their electronic spectra to the visible range and appear colored. For example, oxidative primary intermediates capable of forming colored polymers include materials such as aniline, which has a single functional group and which, on oxidation, forms a series of conjugated imines and quinoid dimers, trimers, etc. ranging in color from green to black. Compounds such as p-phenylenediamine, which has two functional groups, are capable of oxidative polymerization to yield higher molecular weight colored materials having extended conjugated electron systems. Oxidative dyes known in the art can be used in the compositions according to the present invention. A representative list of primary intermediates and secondary couplers suitable for use herein is found in Sagarin, "Cosmetic Science and Technology", *Interscience*, special ed. vol. 2 at pages 308 to 310. It is to be understood that the primary intermediates detailed below are only by way of example and are not intended to limit the compositions and processes herein.

Primary intermediates suitable for use in the compositions and processes herein include: aromatic diamines, polyhydric phenols, amino phenols and derivatives of these aromatic compounds (e.g., N-substituted derivatives of the amines, and ethers of the phenols). Such primary intermediates are generally colorless molecules prior to oxidation.

The typical aromatic diamines, polyhydric phenols, amino phenols, and derivatives thereof, described above as primary intermediates can also have additional substituents on the aromatic ring, e.g. halogen, aldehyde, carboxylic acid, nitro, sulfonic acid and substituted and unsubstituted hydrocarbon groups, as well as additional substituents on the amino nitrogen and on the phenolic oxygen, e.g. substituted and unsubstituted alkyl and aryl groups.

Examples of suitable aromatic diamines and derivatives thereof are compounds having the general formula (A) below. Examples of suitable amino phenols and derivatives thereof are compounds having the general formula (B) below. Examples of suitable polyhydric phenols and derivatives thereof are compounds having the general formula (C) below.

Compounds having the general formula (A) are as follows:

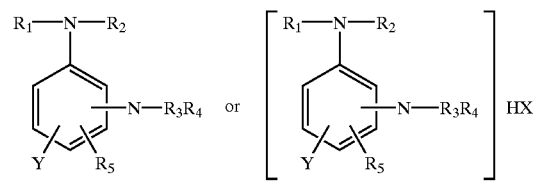

wherein Y is hydrogen, halogen, (e.g. fluorine, chlorine, bromine or iodine), nitro, amino, hydroxyl,

—COOM or —$SO_3M$ (wherein M is hydrogen or an alkali or alkaline earth metal, ammonium, or substituted ammonium (wherein one or more hydrogens on the ammonium ion is replaced with a $C_1$ to $C_3$ alkyl or hydroxyalkyl radical)), wherein $R_1$, $R_2$, $R_3$ and $R_4$ are the same or different from each other and are selected from the group consisting of hydrogen, $C_1$ to $C_4$ alkyl or alkenyl and $C_6$ to $C_9$ aryl, alkaryl or aralkyl, and $R_5$ is hydrogen, $C_1$ to $C_4$ unsubstituted or substituted alkyl or alkenyl, wherein the substituents are selected from those designated as Y, above, or $C_6$ to $C_9$ unsubstituted or substituted aryl, alkaryl or aralkyl wherein the substituents are selected from those defined as Y, above.

The precursors of formula (A) can be used herein in the form of peroxide-compatible salts, wherein X represents peroxide-compatible anions of the type herein before detailed, and wherein Y, $R_1$, $R_2$, $R_3$, $R_4$ and $R_5$ are as designated above. The general formula of the salt indicated is to be understood to encompass those salts having mono-, di-, and tri-negative anions. Specific, non-limiting examples of formula (A) compounds are: o-phenylenediamine, m-phenylenediamine, p- phenylenediamine, 2-chloro-p-phenylenediamine, 2-iodo-p-phenylenediamine, 4-nitro-o-phenylenediamine, 2-nitro-p-phenylenediamine, 1,3,5-triaminobenzene, 2-hydroxy-p-phenylenediamine, 2,4-diaminobenzoic acid, sodium 2,4-diaminobenzoate, calcium di-2,4-diaminobenzoate, ammonium 2,4-diaminobenzoate, trimethylammonium 2,4-, diaminobenzoate, tri-(2-hydroxyethyl) ammonium 2,4-diaminobenzoate, 2,4-diaminobenzaldehyde carbonate, 2,4-diaminobenzensulfonic acid, potassium 2,4-diaminobenzenesulfonate, N,N-diisopropyl-p-, phenylenediamine bicarbonate, N,N-dimethyl-p-phenylenediamine, N-ethyl-N'-(2-propenyl)-p-phenylenediamine, N-phenyl-p-phenylenediamine, N-phenyl-N-benzyl-p-phenylenediamine, N-ethyl-N'-(3-ethylphenyl)-p-phenylenediamine, 2,4-toluenediamine, 2-ethyl-p-phenylenediamine, 2-(2-bromoethyl)-p-phenylenediamine, 2-phenyl-p-phenylenediamine laurate, 4-(2,5-diaminophenyl)-benzaldehyde, 2-benzyl-p-phenylenediamine acetate, 2-(4-nitrobenzyl)-p-phenylenediamine, 2-(4-methylphenyl)-p-phenylenediamine, 2-(2,5-diaminophenyl)-5-methylbenzoic acid, methoxyparaphenylenediamine, dimethyl-p-phenylenediamine, 2,5-dimethylparaphenylene-diamine, 2-methyl-5-methoxy-para-phenylenediamine, 2,6-methyl-5-methoxy-paraphenylenediamine, 3-methyl-4-amino-N,N-diethylaniline, N,N-bis(β-hydroxyethyl)-paraphenylenediamine, 3-methyl-4-amino-N,N-bis(β-hydroxyethyl)aniline, 3-chloro-4-amino-N,N-bis(β-hydroxyethyl)aniline, 4-amino-N-ethyl-N-(carbamethyl)aniline, 3-methyl-4-amino-N-ethyl-N-(carbamethyl)aniline, 4-amino-N-ethyl-(β-piperidonoethyl)aniline, 3-methyl-4-amino-N-ethyl-(β-piperidonoethyl)aniline, 4-amino-N-ethyl-N-(-morpholino-ethyl)aniline, 3-methyl-4-amino-N-ethyl-N-(β-morpholinoethyl)aniline, 4-amino-N-ethyl-N-(β-acetylaminoethyl)aniline, 4-amino-N-(β-methoxyethyl)aniline, 3-methyl-4-amino-N-ethyl-N-(β-acetylaminoethyl)aniline, 4-amino-N-ethyl-N-(β-mesylaminoethyl) aniline, 3-methyl-4-amino-N-ethyl-N-(β-mesylaminoethyl) aniline, 4-amino-N-ethyl-N-(β-sulphoethyl) aniline, 3-methyl-4-amino-N-ethyl-N-(β-sulphoethyl) aniline, N-(4-aminophenyl)-morpholine, N-(4-aminophenyl)piperidine, 2,3-dimethyl-p-phenylenediamine, isopropyl-p-phenylenediamine, N,N-bis-(2-hydroxyethyl)-p-phenylenediamine sulphate.

Compounds having the general formula (B) are as follows:

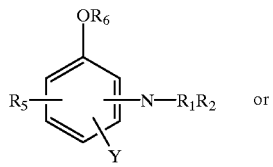

or

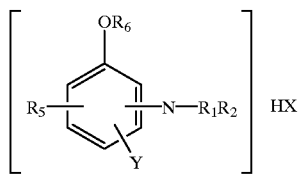

wherein Y is the same as in formula (A), $R_1$ and $R_2$ can be the same or different from each other and are the same as in formula (A), $R_5$ is the same as in formula (A) and $R_6$ is hydrogen or $C_1$ to $C_4$ substituted or unsubstituted alkyl or alkenyl wherein the substituents are selected from those defined as Y in formula (A).

The precursors of formula (B) can be used herein in the form of peroxide-compatible salts, wherein X represents peroxide-compatible anions of the type herein before detailed, and wherein Y, $R_1$, $R_2$, $R_5$, and $R_6$ are as designated above. The general formula of the salt indicated is to be understood to encompass those salts having mono-, di-, and tri-negative anions.

Specific, non-limiting examples of formula (B) compounds are: o-aminophenol, m-aminophenol, p-aminophenol, 2-iodo-p-aminophenol, 2-nitro-p-aminophenol, 3,4-dihydroxyaniline, 3,4-diaminophenol, chloroacetate, 2-hydroxy-4-aminobenzoic acid, 2-hydroxy-4-aminobenzaldehyde, 3-amino-4-hydroxybenzenesulfonic acid, N,N-diisopropyl-p-aminophenol, N-methyl-N-(l-propenyl)-p-aminophenol, N-phenyl-N-benzyl-p-aminophenol sulphate, N-methyl-N-(3-ethylphenyl)-p-aminophenol, 2-nitro-5-ethyl-p-aminophenol, 2-nitro-5-(2-bromoethyl)-p-aminophenol, (2-hydroxy-5-aminophenyl) acetaldehyde, 2-methyl-p-aminophenol, (2-hydroxy-5-aminophenyl)acetic acid, 3-(2-hydroxy-5-aminophenyl)-1-propene, 3-(2-hydroxy-5-aminophenyl)-2-chloro-1-propene, 2-phenyl-p-aminophenol palmitate, 2-(4-nitrophenyl)-p-aminophenol, 2-benzyl-p-aminophenol, 2-(4-chlorobenzyl-p-aminophenol perchlorate, 2-(4-methylphenyl)-p-aminophenol, 2-(2-amino-4-methylphenyl)-p-aminophenol, p-methoxyaniline, 2-bromoethyl-4-aminophenyl ether phosphate, 2-nitroethyl-4-aminophenyl ether bromide, 2-aminoethyl-4-aminophenyl ether, 2-hydroxyethyl-4-aminophenyl ether, (4-aminophenoxy)acetaldehyde, (4-aminophenoxy)acetic acid, (4-aminophenoxy)methanesulfonic acid, 1-propenyl-4-aminophenyl ether isobutyrate, (2-chloro)-1-propenyl-4-aminophenyl ether, (2-nitro)-1-propenyl-4-aminophenyl ether, (2-amino)-propenyl-4-aminophenyl ether, (2-hydroxy)-1-propenyl-4-aminophenyl ether, N-methyl-p-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 3-hydroxymethyl-4-aminophenol, 2,6-dichloro-4-aminophenol, 2,6-dibromo-4-aminophenol and 2-bromo-4-aminophenol.

Compounds having the general formula (C) are as follows:

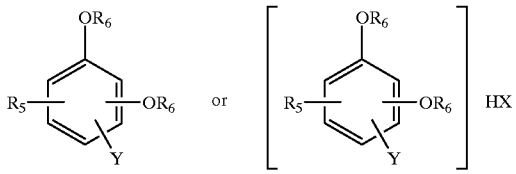

wherein Y is the same as in formula (A), $R_5$ is the same as in formula (A) and $R_6$ is hydrogen or $C_1$ to $C_4$ substituted or unsubstituted alkyl or alkenyl wherein the substituents are selected from those defined as Y in formula (A).

The precursors of formula (C) can be used herein in the form of peroxide-compatible salts, wherein X represents peroxide-compatible anions of the type herein before detailed, and wherein Y, $R_5$ and $R_5$ are as designated above. The general formula of the salt indicated is to be understood to encompass those salts having mono-, di-, and tri-negative anions.

Specific examples of formula (C) compounds are: o-hydroxyphenol (catechol), m-hydroxyphenol (resorcinol), p-hydroxyphenol (hydroquinone), 4-methoxyphenol, 2-methoxyphenol, 4-(2-chloroethoxy) phenol, 4-(2-propenoxy) phenol, 4-(3-chloro-2-propenoxy) phenol, 2-chloro-4-hydroxyphenol (2-chlorohydroquinone), 2-nitro-4-hydroxyphenol(2-nitrohydroquinone), 2-amino-4-hydroxyphenol, 1,2,3-trihydroxybenzene (pyrogallol), 2,4-dihydroxybenzaldehyde, 3,4-dihydoxybenzoic acid, 2,4-dihydroxybenzenesulfonic acid, 3-ethyl-4-hydroxyphenol, 3-(2-nitroethyl)-4-hydroxyphenol, 3-(2-propenyl)-4-hydroxyphenol, 3-(3-chloro-2-propenyl)-4-hydroxyphenol, 2-phenyl-4-hydroxyphenol, 2-(4-chlorophenyl)-4-hydroxyphenol, 2-benzyl-4-hydroxyphenol, 2-(2-nitrophenyl)-4-hydroxyphenol, 2-(2-methylphenyl)-4-hydroxyphenol, 2-(2-methyl-4-chlorophenyl)-4-hydroxyphenol, 3-methoxy-4-hydroxy-benzaldehyde, 2-methoxy-4-(1-propenyl)phenol, 4-hydroxy-3-methoxycinnamic acid, 2,5-dimethoxyaniline, 2-methylresorcinol, alpha napthol and salts thereof.

Additional primary intermediates suitable for use herein include catechol species and in particular catechol "dopa" species which includes dopa itself as well as homologs, analogs and derivatives of DOPA. Examples of suitable cachetol species include cysteinyl dopa, alpha alkyl dopa having 1 to 4, preferably 1 to 2 carbon atoms in the alkyl group, epinephrine and dopa alkyl esters having 1 to 6, preferably 1 to 2 carbon atoms in the alkyl group.

In general suitable catechols are represented by formula (D) below:

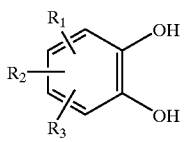

wherein $R_1$, $R_2$ and $R_3$, which may be the same or different, are electron donor or acceptor substituents selected from H, $C_1$ to $C_6$ alkyl, OH, OR, COOR, NHCOR, CN, COOH, halogen, $NO_2$, $CF_3$, $SO_3H$ or $NR_4R_5$, with the proviso that only one of the $R_1$, $R_2$ or $R_3$ can be CN, COOH, halogen, $NO_2$, $CF_3$ or $SO_3H$, and that $R_4$ and $R_5$, which may be the same or different, are H, $C_1$ to $C_6$ alkyl or substituted $C_1$ to $C_6$ alkyl in which the substituent may be OH, OR, $NHCOR_6$, $NHCONH_2$, $NHCO_2R_6$, $NHCSNH_2$, CN, COOH, $SO_3H$, $SO_2NR_6$, $SO_2R_6$ or $CO_2R_6$; $R_6$ is $C_1$ to $C_6$ alkyl, $C_1$ to $C_6$ hydroxyalkyl phenyl linked to the nitrogen by an alkylene chain, phenyl or substituted phenyl with the substituent defined as $R_1$, and R is $C_1$ to $C_6$ alkyl or $C_1$ to $C_6$ hydroxyalkyl.

Also included herein are oxidative hair coloring agents represented by the general formula (E):

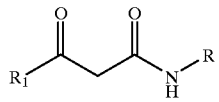

wherein: $R_1$=substituted or unsubstituted benzene ring, tertiary-butyl, etc.; R=substituted or unsubstituted benzene ring; and oxidative hair coloring agents represented by the general formula (F):

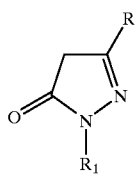

wherein R=aminoalkyl, amidoalkyl, aminobenzene (substituted or unsubstituted), amidobenzene (substituted or unsubstituted), alkyl, substituted or unsubstituted benzene ring; and $R_1$=substituted or unsubstituted benzene ring.

Also suitable for use herein are hydroxyindole dye precursors, such as those described by Repligen Corp. in EP 0,271,186A1, which description is incorporated herein by reference. Preferred hydroxyindoles include: 5,6-dihydroxyindole, 4-hydroxyindole, 5-hydroxyindole, 6-hydroxyindole, 7-hydroxyindole, 5-hydroxyindole-3-acetic acid, 5-hydroxyindole-2-carboxylic acid, 5-hydroxy-3-hydroxyethyl-indole, 5-hydroxy-2-hydroxymethyl-indole, and mixtures thereof.

b. Secondary Intermediates (couplers)

Secondary coupling compounds which are suitable for inclusion in the hair bleaching and coloring compositions and processes herein before described include certain aromatic amines and phenols and derivatives thereof which do not produce color singly, but which modify the color, shade or intensity of the colors developed by the primary oxidized dye intermediates. Certain aromatic amines and phenolic compounds, and derivatives thereof, including some aromatic diamines and polyhydric phenols of the types described by formulas (A), (B) and (C) above, but which are well known in the art not to be suitable primary intermediates, are suitable as couplers herein. Polyhydric alcohols are also suitable for use as couplers herein.

The aromatic amines and phenols and derivatives described immediately above as couplers can also have additional substituents on the aromatic ring, e.g., halogen, aldehyde, carboxylic acid, nitro, sulfonyl and substituted and unsubstituted by hydrocarbon groups, as well as additional substituents on the amino nitrogen, or phenolic oxygen, e.g. substituted and unsubstituted alkyl and aryl groups. Again, peroxide-compatible salts thereof are suitable for use herein.

Examples of aromatic amines, phenols and derivatives thereof are compounds of the general formulae (G) and (H) below.

Compounds having the general formula (G) are as follows:

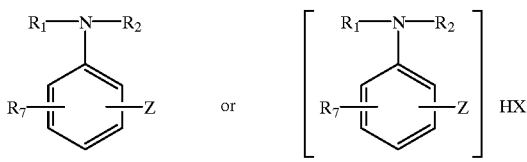

wherein Z is hydrogen, $C_1$ or $C_3$ alkyl, halogen (e.g. fluorine, chlorine, bromine or iodine) nitro,

—COOM or $SO_3M$, (wherein M is hydrogen or an alkali or alkaline earth metal, ammonium or substituted ammonium (wherein one or more hydrogens on the ammonium ion is replaced with a 1 to 3 carbon atom alkyl or hydroxyalkyl radical)), wherein $R_1$ and $R_2$ are the same or different and are selected from the group consisting of hydrogen, $C_1$ to $C_4$ alkyl or alkenyl and $C_6$ or $C_9$ aryl, alkaryl or aralkyl and $R_7$ is hydrogen, $C_1$ to $C_4$ unsubstituted or substituted alkyl or alkenyl wherein the substituents are selected from those designated as Z above or $C_6$ to $C_9$ unsubstituted or substituted aryl, alkaryl or aralkyl wherein the substituents are selected from those defined as Z above and wherein X is as defined in formula (A).

Specific examples of formula (G) compounds are: aniline, p-chloroaniline, p-fluoroaniline, p-nitroaniline, p-aminobenzaldehyde, p-aminobenzoic acid, sodium-p-aminobenzoate, lithium-p-aminobenzoate, calcium di-p-aminobenzoate, ammonium-p-aminobenzoate, trimethylammonium-p-aminobenzoate, tri(2-hydroxyethyl)-p-aminobenzoate, p-aminobenzene-sulfonic acid, potassium p-aminobenzenesulfonate, N-methylaniline, N-propyl-N-phenylaniline, N-methyl-N-2-propenylaniline, N-benzylaniline, N-(2-ethylphenyl)aniline, 4-methylaniline, 4-(2-bromoethyl)aniline, 2-(2-nitroethyl)aniline, (4-aminophenyl)acetaldehyde, (4-aminophenyl)acetic acid, 4-(2-propenyl)aniline acetate, 4-(3-bromo-2-propenyl)aniline, 4-phenylaniline chloroacetate, 4-(3-chlorophenyl)aniline, 4-benzylaniline, 4-(4-iodobenzyl)aniline, 4-(3-ethylphenyl)aniline, 4-(2-chloro-4-ethylphenyl)aniline.

Compounds having the general formula (H) are as follows:

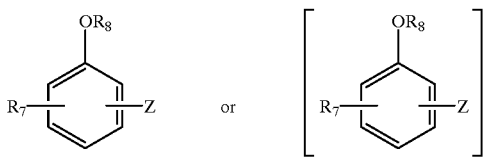

wherein Z and $R_7$ are defined as in formula (G) and $R_8$ is hydrogen or $C_1$ to $C_4$ substituted or unsubstituted alkyl or alkenyl wherein the substituents are selected from those defined as Z in formula (G).

Specific examples of formula (H) compounds are: phenol, p-chlorophenol, p-nitrophenol, p-hydroxybenzaldehyde, p-hydroxybenzoic acid, p-hydroxybenzenesulfonic acid, ethylphenyl ether, 2-chloroethylphenyl ether, 2-nitroethylphenyl ether, phenoxyacetaldehyde, phenoxyacetic acid, 3-phenoxy-1-propene, 3-phenoxy-2-nitro-1-propene, 3-phenoxy-2-bromo-1-propene, 4-propylphenol, 4-(3-bromopropyl)phenol, 2-(2-nitroethyl)phenol, (4-hydroxyphenyl)acetaldehyde, (4-hydroxyphenyl)acetic acid, 4-(2-propenyl)phenol, 4-phenylphenol, 4-benzylphenol, 4-(3-fluoro-2-propenyl)phenol, 4-(4-chlorobenzyl)phenol, 4-(3-ethylphenyl)phenol, 4-(2-chloro-3-ethylphenyl)phenol, 2,5-xylenol, 2,5-diaminopyridine, 2-hydroxy-5-aminopyridine, 2-amino-3-hydroxy pyridine, tetraaminopyrimindine, 1,2,4-trihydroxybenzene, 1,2,4-trihydroxy-5-($C_1$–C6-alkyl)benzene, 1,2,3-trihydroxybenzene, 4-aminoresorcinol, 1,2-dihydroxybenzene, 2-amino-1,4-dihydroxybenzene, 2-amino-4-methoxyphenol, 2,4-diaminophenol, 3-methoxy-1,2-dihydroxy-benzene, 1,4-dihydroxy-2-(N,N-diethylamino)benzene, 2,5-diamino-4-methoxy-1-hydroxybenzene, 4,6-dimethoxy-3-amino-1-hydroxybenzene, 2,6-dimethyl-4-[N-(p-hydroxyphenyl)amino]-1-hydroxybenzene, 1,5-diamino-2-methyl-4-[N-(p-hydroxyphenyl)amino]benzene and salts thereof.

c. Color, Shade, and Intensity

The primary intermediates can be used herein alone or in combination with other primary intermediates, and one or more can be used in combination with one or more couplers. The choice of primary intermediates and couplers will be determined by the color, shade and intensity of coloration which is desired. There are several preferred primary intermediates and couplers which can be used herein, singly or in combination, to provide dyes having a variety of shades ranging from ash blonde to black, including: pyrogallol, resorcinol, p-toluenediamine, p-phenylenediamine, o-phenylenediamine, m-phenylenediamine, o-aminophenol, p-amino-phenol, 4-amino-2-nitrophenol, nitro-p-phenylenediamine, N-phenyl-p-phenylenediamine, m-aminophenol, 2-amino-3-hydroxypyridine, 1-napthol, N,N-bis-(2-hydroxyethyl)-p-phenylenediamine, 4-amino-2-hydroxytoluene, 1,5-dihydroxynapthalene, 2-methyl resorcinol 2,4-diaminoanisole, 4-amino-m-cresol, 2,4 diaminophenoxyethanol HCl, 3,4-methylenedioxyphenol, 1,5-dihydroxynaphthalene, 1,7-dihydroxynaphthalene, 4-chlororesorcinol, 2,4,5,6-tetraaminopyrimidine sulfate, 2,6-dihydroxy-3,4-dimethylpyridine, 1,3-bis-(2,4-diaminophenoxy)-propane, 5-amino-6-chloro-o-cresol, and mixtures thereof. These can be used in the molecular form or in the form of peroxide-compatible salts, as detailed above.

Also preferred are photo-oxidative intermediates, including: 4-amino-2,6-dibromophenol, 4-amino-2,6-dichlorophenol, 1,3-dimethylpyrazolinone, 3-methyl-1-phenylpyrazolinone, 3-methylpyrazolinone, N,N-dimethylacetoacetamide, N,N-diethylacetoacetamide, 3-amino-phenol, 1-naphthol, and those pyrazolazoles represented by the following general formula (J):

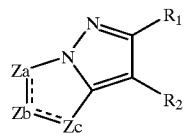

wherein Za, Zb and Zc are either nitrogen or carbon, which in turn, can be further substituted by hydrogen, methyl or other groups; $R_1$ and $R_2$ are independently H, alkyl, benzyl, nitrogen based, halogen, or sulphur based substituents.

For example, low intensity colors such as natural blond to light brown hair shades generally comprise from about 0.001% to about 5%, preferably from about 0.1% to about 2%, more preferably from about 0.2% to about 1% by weight of coloring composition of total oxidative dyeing agents and may be achieved by the combination of primary intermediates such as 1,4-diamino-benzene, 2,5-diamino toluene, 2,5-diamino-anisole, 4-aminophenol, 2,5-diamino-benzyl alcohol and 2-(2',5'-diamino)phenyl-ethanol with couplers such as resorcinol, 2-methyl resorcinol or 4-chloro resorcinol.

Similarly, combination of the above primary intermediates with couplers, such as, 5-amino-2-methyl phenol and 1,3-diamino-benzene derivatives such as 2,4-diamino-anisole at levels of from about 0.5% to about 1% of total dyeing agents can lead to medium intensity red colors. High intensity colors such as blue to blue-violet hair shades can be produced by the combination of the above primary intermediates with couplers such as 1,3-diamino-benzene or its derivatives such as 2,5-diamino-toluene at levels of from about 1% to about 6% by weight of composition of total dyeing agents. Black hair colors can be obtained by combining the aforementioned primary intermediates with couplers such as 1,3-diaminobenzene or its derivatives 2. Non-oxidative and Other Dyes The stable alkaline hair bleaching compositions of the present invention may, in addition to or instead of an oxidative hair coloring agent, include non-oxidative and other dye materials. Such non-oxidative and other dyes suitable for use in the hair coloring compositions and processes according to the present invention include both semi-permanent, temporary and other dyes. Non-oxidative dyes as defined herein include the so-called 'direct action dyes', metallic dyes, metal chelate dyes, fibre reactive dyes and other synthetic and natural dyes. Various types of non-oxidative dyes are detailed in: *Chemical and Physical Behaviour of Human Hair* 3rd ed. Clarence Robbins (at pages 250–259); *The Chemistry and Manufacture of Cosmetics*. vol. IV. 2nd ed. Maison G. De Navarre (at chapter 45 by G. S. Kass (at pages 841–920)); *Cosmetics: Science and Technology* 2nd ed., vol. II Balsam Sagarin, (at chapter 23 by F. E. Wall (at pages 279–343)); *The Science of Hair Care*, edited by C. Zviak (at pages 235–261) and *Hair Dyes*, J. C. Johnson, Noyes Data Corp., Park Ridge, U.S.A. (1973), (at pages 3–91 and 113–139).

a. Direct Action Dyes

The stable alkaline hair bleaching compositions of the present invention may employ direct action dyes. Also known as hair tints, such dyes do not require an oxidative effect in order to develop the color, and have long been known in the art. They are usually applied to the hair in a base matrix which includes surfactant material. Direct action dyes include nitro dyes such as the derivatives of nitroamino benzene or nitroaminophenol; disperse dyes such as nitroaryl amines, aminoanthraquinones or azo dyes; anthraquinone dyes, naphthoquinone dyes; basic dyes such as Acridine Orange C.I. 46005.

Further examples of direct action dyes include the Arianor dyes basic brown 17, C.I.(color index)-no. 12,251; basic red 76, C.I.-12,245; basic brown 16, C.I.-12,250; basic yellow 57, C.I.-12,719 and basic blue 99, C.I.-56,059 and further direct action dyes such as acid yellow 1, C.I.-10,316 (D&C yellow no.7); acid yellow 9, C.I.-13,015; basic violet C.I.-45,170; disperse yellow 3, C.I.-11,855; basic yellow 57, C.I.-12,719; disperse yellow 1, C.I.-10,345; basic violet 1, C.I.-42,535, basic violet 3, C.I.-42,555; greenish blue, C.I.-42090 (FD&C Blue no.1); yellowish red, C.I.-14700 (FD&C red no.4); yellow, C.I.19140 (FD&C yellow no5); yellowish orange, C.I.15985 (FD&C yellow no.6); bluish green, C.I.42053 (FD&C green no.3); yellowish red, C.I.16035 (FD&C red no.40); bluish green, C.I.61570 (D&C green no.3); orange, C.I.45370 (D&C orange no.5); red, C.I.15850 (D&C red no.6); bluish red, C.I.15850(D&C red no.7); slight bluish red, C.I.45380(D&C red no.22); bluish red, C.I.45410(D&C red no.28); bluish red, C.I.73360 (D&C red no.30); reddish purple, C.I.17200(D&C red no.33); dirty blue red, C.I.15880(D&C red no.34); bright yellow red, C.I.12085(D&C red no.36); bright orange, C.I.15510(D&C orange no.4); greenish yellow, C.I.47005 (D&C yellow no.10); bluish green, C.I.59040(D&C green no.8); bluish violet, C.I.60730(Ext. D&C violet no.2); greenish yellow, C.I.10316(Ext. D&C yellow no.7).

Also suitable for use herein are the cationic direct action dyes described by L'Oreal in French Pat. No. 2,974,645, in EP 0,850,638A1, and in EP 0,923,929A1, all of which descriptions are incorporated herein by reference.

b. Fiber Reactive Dyes, Natural Dyes, and Metallic Dyes

The stable alkaline hair bleaching compositions of the present invention may comprise fiber reactive dyes and natural dyes. Suitable fiber reactive dyes for use herein include those described in *The Theory of Coloration of Textiles*, $2^{nd}$ ed. (Alan Johnson, editor), published by Society of Dyers and Colourists, 1989, at pages 99–103, which description is incorporated herein by reference. Preferred fiber reactive dyes include the Procion®, Drimarene®, Cibacron®, Levafix® and Remazol® dyes available from ICI, Sandoz, Ciba-Geigy, Bayer and Hoechst respectively.

Natural dyes and vegetable dyes suitable for use herein include: henna (*Lawsonia alba*) wherein the active ingredient is 2-hydroxy-1,4-naphtoquinone; chamomile (*Matricaria chamomila* or *Anthemis nobilis*) wherein the active ingredient is 4',5,7-trihydroxyflavone; indigo (Indigofera family); extracts logwood, walnut hull, and nutgall. Metallized dyes suitable for use herein include: salts of silver, copper, nickel, bismuth, cobalt, and manganese. All of these natural dyes, vegetable dyes, and metallized dyes are described in *The Science of Hair Care*, (Charles Zviak, editor), published by Marcel Dekker, Inc., 1986, at pages 238–241, which description is incorporated herein by reference.

Also suitable for use herein are vat dyes, which although they are practically insoluble in water, can be transformed by reduction (vatting) into compounds (in the "leuco" form) which are soluble in aqueous alkali and dyed in this form. Also suitable for use herein are sulfur dyes, which are obtained by treating aromatic amines, phenols, and aminophenols with sulfur or sodium polysulfide or both. Such vat dyes and sulfur dyes are described at pages 232–233 and 249–250, respectively, in *Color Chemistry: Syntheses, Properties and Applications of Organic Dyes and Pigments*, $2^{nd}$ ed. (Heinrich Zollinger), published by VCH Verlagsgesellschaft mbH, 1991, which descriptions are incorporated herein by reference.

Also suitable for use herein are melanin-type dyes, such as those described by Briston-Myers Squibb in WO 93/05, 759, which description is incorporated herein by reference.

c. Temporary Hair Dyes

Temporary hair dyes, or hair coloring rinses, are generally comprised of dye molecules which are too large to diffuse into the hair shaft and which act on the exterior of the hair. They are usually applied via a leave-in procedure in which the dye solution is allowed to dry on the hair surface. As such these dyes are typically less resistant to the effects of washing and cleaning the hair with surface active agents and are washed off of the hair with relative ease. Any temporary hair dye may suitably be used in the compositions of the invention and examples of preferred temporary hair dyes are illustrated below.

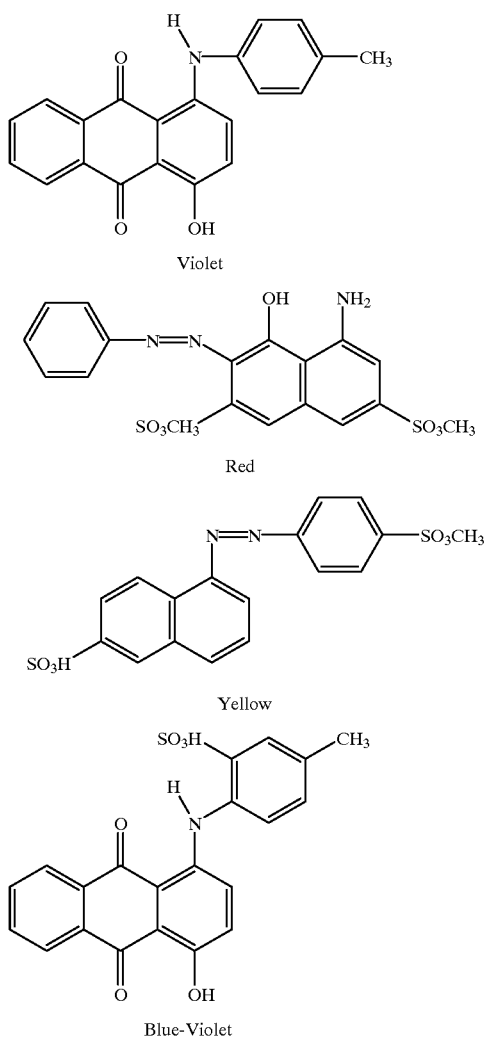

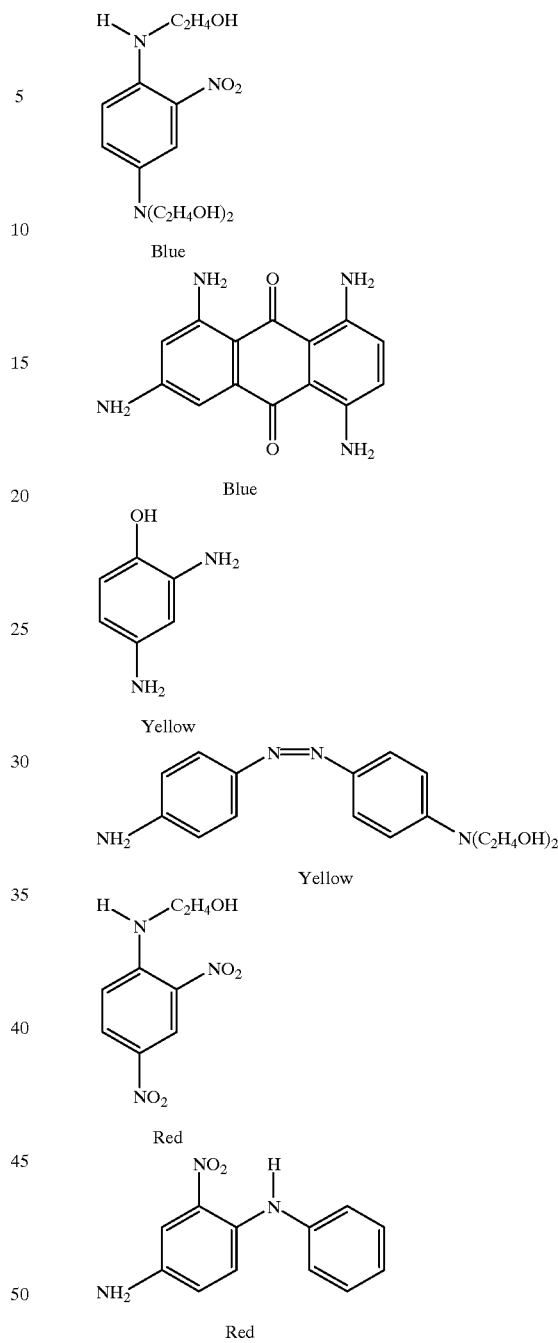

d. Semi-permanent Hair Dyes

Semi-permanent hair dyes are dyes which are generally smaller in size and effect to temporary hair rinses but are generally larger than permanent (oxidative) dyes. Typically, semi-permanent dyes act in a similar manner to oxidative dyes in that they have the potential to diffuse into the hair shaft. However, semi-permanent dyes are generally smaller in size than the aforementioned conjugated oxidative dye molecules and as such are pre-disposed to gradual diffusion out of the hair again. Simple hair washing and cleaning action will encourage this process and in general semi-permanent dyes are largely washed out of the hair after about 5 to 8 washes. Any semi-permanent dye system may be suitably used in the compositions of the present invention. Suitable semi-permanent dyes for use in the compositions of the present invention are HC Blue 2, HC Yellow 4, HC Red 3, Disperse Violet 4, Disperse Black 9, HC Blue 7, HC Yellow 2, Disperse Blue 3, Disperse violet 1 and mixtures thereof. Examples of semi-permanent dyes are illustrated below:

Typical semi-permanent dye systems incorporate mixtures of both large and small color molecules. As the size of the hair is not uniform from root to tip the small molecules will diffuse both at the root and tip, but will not be retained within the tip, while the larger molecules will be generally only be able to diffuse into the ends of the hair. This combination of dye molecule size is used to help give consistent color results from the root to the tip of the hair both during the initial dyeing process and during subsequent washing.

B. Diluent

The stable alkaline hair bleaching compositions of the present invention may comprise a diluent. Where present, the preferred diluent for the compositions of the present invention is water. However, these compositions may include one or more solvents as additional diluent materials. Generally, solvents suitable for use in the coloring compositions of the present invention are selected to be miscible with water and innocuous to the skin. Solvents suitable for use as additional diluents herein include $C_1$ to $C_{20}$ mono- or polyhydric alcohols and their ethers, glycerine, with monohydric and dihydric alcohols and their ethers preferred. In these compounds, alcoholic residues containing 2 to 10 carbon atoms are preferred. Thus, a preferred group includes ethanol, isopropanol, n-propanol, butanol, propylene glycol, ethylene glycol monoethyl ether, and mixtures thereof. Water is the preferred principal diluent in the compositions according to the present invention. Principal diluent, as defined herein, means, that the level of water present is higher than the total level of any other diluents.

The diluent is present at a level preferably of from about 5% to about 99.98%, preferably from about 15% to about 99.5%, more preferably at least from about 30% to about 99%, and especially from about 50% to about 98% by weight of the compositions herein.

C. Enzyme

The stable alkaline hair bleaching compositions of the present invention, may in some embodiments, further comprise one or more enzymes. Enzymes are optionally incorporated at levels sufficient to provide up to about 50 mg by weight, more typically about 0.01 mg to about 10 mg of active enzyme per gram of the hair treatment composition of the invention. Stated another way, the enzyme may be incorporated into the compositions in accordance with the invention at a level from about 0.0001% to about 5% active enzyme, by weight of the composition, preferably from about 0.001% to about 1%, more preferably from about 0.01% to about 1%. Suitable enzymatic materials include the commercially available lipases, cutinases, amylases, neutral and alkaline proteases, esterases, cellulases, pectinases, lactases and peroxidases conventionally incorporated into detergent compositions. Suitable enzymes are discussed in U.S. Pat. Nos. 3,519,570 and 3,533,139, both of which descriptions are incorporated herein by reference.

1. Peroxidase

Peroxidases are haemoproteins specific for peroxide, but using a wide range of substances as donors. Catalase which decomposes peroxide, is included here in view of the fact that it is generally similar in structure and properties and is able to bring about certain oxidations by $H_2O_2$. The decomposition of $H_2O_2$ can be regarded as the oxidation of one molecule by the other. It is widespread in aerobic cells and may have some more important function. The coenzyme peroxidases are not haemoproteins and one at least is a flavoprotein. Other flavoproteins such as xanthine oxidase will also use $H_2O_2$ among other acceptors, and the coenzyme peroxidases resemble these rather than the classical peroxidases in not being specific for $H_2O_2$. Suitable peroxidases for the compositions of the present invention include horseradish peroxidase, Japanese radish peroxidase, cow's milk peroxidase, rat liver peroxidase, linginase and haloperoxidase such as chloro- and bromo-peroxidase.

2. Protease

Commercially available protease enzymes include those sold under the tradenames Alcalase, Savinase, Primase, Durazym, and Esperase by Novo Industries A/S (Denmark), those sold under the tradenames Maxatase, Maxacal and Maxapem by Gist-Brocades, those sold by Genencor International, and those sold under the tradenames Opticlean and Optimase by Solvay Enzymes. Protease enzyme may be incorporated into the compositions in accordance with the invention at a level of from 0.0001% to 4% active enzyme by weight of the composition.

3. Amylase

Amylases include, for example, α-amylases obtained from a special strain of *B. licheniformis*, described in more detail in GB-1,269,839 (Novo), which description is incorporated herein by reference. Preferred commercially available amylases include for example, those sold under the tradename Rapidase by Gist-Brocades, and those sold under the tradenames Termamyl and BAN by Novo Industries A/S. Amylase enzyme may be incorporated into the composition in accordance with the invention at a level of from 0.0001% to 2% active enzyme by weight of the composition.

4. Lipase

Lipolytic enzyme may be present at levels of active lipolytic enzyme of from 0.0001% to 2% by weight, preferably 0.001% to 1% by weight, most preferably from 0.001% to 0.5% by weight of the compositions.

The lipase may be fungal or bacterial in origin being obtained, for example, from a lipase producing strain of Humicola sp., Thermomyces sp. or Pseudomonas sp. including *P. pseudoalcaligenes* or *P. fluorescens*. Lipase from chemically or genetically modified mutants of these strains are also useful herein. A preferred lipase is derived from *P. pseudoalcaligenes*, which is described in Granted European Patent, EP-B-0218272, which description is incorporated herein by reference.

Another preferred lipase herein is obtained by cloning the gene from *Humicola lanuginosa* and expressing the gene in *Aspergillus oryza*, as host, as described in European Patent Application, EP-A-0258 068 (which description is incorporated herein by reference), which is commercially available from Novo Industri A/S, Bagsvaerd, Denmark, under the tradename Lipolase. This lipase is also described in U.S. Pat. No. 4,810,414, which description is incorporated herein by reference.

5. Oxido-reductase

Enzymes of the oxido-reductase type may be used in the compositions herein. A preferred oxido-reductase is laccase, and a preferred laccase is uricase. Suitable for use herein are those oxido-reductases described by L'Oreal in WO 99/20,236, which description is incorporated herein by reference. Suitable for use herein are those laccases described by L'Oreal in WO 99/36,041, which description is incorporated herein by reference.

D. pH Modifiers

Several different pH modifiers may be used to adjust the pH of the final composition or any constituent part thereof. This pH adjustment can be effected by using well known acidifying agents in the field of treating keratinous fibers, and in particular human hair, such as inorganic and organic acids. Such pH modifiers should be physically and chemically compatible with the essential components of the composition, particularly the buffering system, and should not otherwise unduly impair product stability, aesthetics or performance.

Non-limiting examples of pH modifiers include: hydrochloric acid, tartaric acid, citric acid, phosphoric acid and carboxylic or sulfonic acids such as ascorbic acid, acetic acid, lactic acid, sulfuric acid, formic acid, ammonium sulfate and sodium dihydrogenphosphate/phosphoric acid, disodium hydrogenphosphate/phosphoric acid, potassium chloride/hydrochloric acid, potassium dihydrogen phthalate/hydrochloric acid, sodium citrate/hydrochloric acid, potassium dihydrogen citrate/hydrochloric acid, potassium dihydrogencitrate/citric acid, sodium citrate/citric acid, sodium tartarate/tartaric acid, sodium lactate/lactic acid, sodium acetate/acetic acid, disodium hydrogenphosphate/citric acid and sodium chloride/glycine/hydrochloric acid and mixtures thereof.

E. Other Optional Components

A number of additional optional materials can be added to the coloring compositions herein described each at a level of from about 0.001% to about 5%, preferably from about 0.01% to about 3%, more preferably from about 0.05% to about 2% by weight of composition. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl® K400, natural preservatives such as benzyl alcohol, potassium sorbate and bisabalol, benzoic acid, sodium benzoate and 2-phenoxyethanol; anti-oxidants such as sodium sulphite, hydroquinone, sodium bisulphite, sodium metabisulphite and thyoglycolic acid, sodium dithionite, erythrobic acid and other mercaptans, which such anti-oxidants may be delivered using encapsulation techniques described in U.S. Pat. No. 5,053,051 (Goldwell), which description is incorporated herein by reference; dye removers such as oxalic acid, sulphated castor oil, salicylic acid and sodium thiosulphate; $H_2O_2$ stabilizers, in addition to the aminomethylene phosphonic acid stabilizers of the present invention, such as tin compounds such as sodium stannate, stannic hydroxide and stannous octoate, acetanilide, phenacetin colloidal silica such as magnesium silicate, oxyquinoline sulphate, sodium phosphate, and tetrasodium pyrophosphate; and p-hydroxybenzoates; moisturizing agents such as hyaluronic acid, chitin, and starch-grafted sodium polyacrylates such as Sanwet® IM-1000, IM-1500 and IM-2500 available from Celanese Superabsorbent Materials, Portsmith, Virginia, USA, and described in U.S. Pat. No. 4,076,663, which description is incorporated herein by reference; as well as methyl cellulose, starch, higher fatty alcohols, paraffin oils, fatty acids and the like; solvents, in addition to the aforementioned diluents; anti-bacterial agents such as Oxeco (phenoxy isopropanol); low temperature phase modifiers such as ammonium ion sources (e.g. $NH_4Cl$); viscosity control agents such as magnesium sulfate and other electrolytes; quaternary amine compounds such as distearyl-, dilauryl-, di-hydrogenated beef tallow-, dimethyl ammonium chloride, dicetyldiethyl ammoniumethylsulphate, ditallowdimethyl ammonium methylsulphate, disoya dimethyl ammonium chloride and dicoco dimethyl ammonium chloride; enzyme stabilizers such as water soluble sources of calcium or borate species; coloring agents in addition to those aforementioned oxidative and non-oxidative coloring agents; $TiO_2$ and $TiO_2$-coated mica; perfumes and perfume solubilizers; and zeolites such as Valfour BV400 and derivatives thereof; and water softening agents, such as sodium citrate.

III. Methods of Manufacture

The stable alkaline hair bleaching compositions of the present invention may be prepared by any known or otherwise effective technique, suitable for providing a hair bleaching and/or coloring composition provided that the resulting composition provides the longer shelf-longevity and simpler and fewer solutions benefits described herein. Furthermore, it is important that these compositions are in a delivery form which is easy and convenient to prepare and use by the consumer, since the oxidizing agent must remain in contact with the hair for a certain period of time and not run or drip off of the hair, possibly causing eye or skin irritation.

A typical method of preparing the stable alkaline hair bleaching compositions of the present invention may include the following steps. (1) Generally any surfactant, conditioning ingredients, thickeners, and the like, are melted and/or pre-solubilized in a diluent at about 60° C. to about 80° C. to create a main emulsion phase. (2) Separately, a secondary phase containing the oxidant and stabilizing and buffer components is prepared at about 20° C. to about 40° C. Most other components, such as the catalyst, enzyme, preservatives, antioxidants, perfumes, and the like are mixed into this phase. (3) The main emulsion phase is then cooled to about 20° C. to about 40° C., followed by admixing with the secondary phase. (4) Finally, pH adjustments are made.

A typical method of preparing the stable alkaline hair bleaching and coloring compositions of the present invention may be similar to the steps described above for bleaching only compositions, with these modifications. If non-oxidative dyes are used, then a tertiary phase containing the non-oxidative dyes is prepared with the appropriate diluent and added to the above described main emulsion phase at about 40° C. to about 60° C. so that non-oxidative dyes, oxidant and stabilizers and others are present in a single bottle.

If oxidative dyes are used, then the above steps for the bleaching composition only are completed for the bleaching composition and the "dye/color composition" is manufactured separately as follows: (a) Generally any surfactant, conditioning ingredients, thickeners, and the like, are melted and/or pre-solubilized in a diluent at about 60° C. to about 80° C. to create a main emulsion phase; (b) Separately, multiple secondary phases containing the different oxidative dyes and diluents are prepared at about 40° C. to about 80° C. (c) As the main emulsion phase is cooled, then most other components: dye premixes/secondary phases, buffers, catalyst, enzyme, preservatives, antioxidants, perfumes, and the like are mixed into this phase and cooled to room temperature. (d) Finally, pH adjustments are made.

The stable alkaline bleaching compositions of the present invention may be provided in both a single pack or in kit form as separately packaged components. Where only bleaching of the hair is desired or where bleaching and coloring with a non-oxidative coloring agent is desired, there will typically be a single solution. Where bleaching and coloring with an oxidative coloring agent is desired, there will typically be two solutions, wherein the solutions are either mixed by the user immediately prior to application to the hair, or mixed and stored for future use, or mixed and partly used and the remainder stored for future use.

As hereinbefore described, the compositions according to the present invention may be used by the consumer as a single component package. Such a single pack would comprise a single solution a pH from about 5 to about 11 containing both an oxidizing agent and non-oxidative dyes. The solution would be applied directly to the hair by the consumer without the need for any pretreatments or mixing thereby providing a simple, fast, easy to use, 'no-mess' hair coloring system. A further advantage of such a single component system is that it could be stored and reused i.e., a single package could contain enough coloring composition for several applications over time.

Alternatively, the compositions according to the present invention can be packaged as follows: one component of the kit comprises an individually packaged oxidizing component while further kit components could comprise an oxidative coloring agent mixture or two separate individual packages of oxidizing agents and oxidative coloring agents.

I. A hair coloring kit is assembled comprising a single package including therein: (1) a bottle of an oxidizing solution (e.g. 3%, by weight, hydrogen peroxide), a buffering system (e.g. 0.2%, by weight, of a borates buffer and 2.5%, by weight, ammonium hydroxide) and optionally buffering agents and/or stabilizers; and (2) a 50 ml bottle containing one or more oxidative hair coloring agents and, optionally, additional agents such as surfactants, stabilizers, buffering agents, antioxidants, thickeners etc. The oxidative hair coloring agents can either be admixed with the hydrogen peroxide to form the dyeing system of the present invention and the resulting solution can be either applied to the hair to color it or stored for future use, or the separately packaged stable components can be stored and mixed when required.

II. A hair coloring kit as described above wherein the hydrogen peroxide containing component is applied to the hair prior to application of the oxidative hair coloring agents and additional materials to the hair.

III. Further examples of kit components for the hair coloring compositions according to the present invention include separately packaged oxidant and oxidative hair coloring agents wherein either one or both components are present in particulate form.

IV. Methods of Use

The stable alkaline hair bleaching compositions of the present invention may be applied to directly to the hair or via some vehicle, such as brushes, combs, applicators, or other beautifying tools, by the consumer or by a stylist, and may be applied to both wet and dry hair. As noted above, it is important that dyeing compositions be in a form which is easy and convenient to prepare and use by the consumer, since the oxidizing agent must remain in contact with the hair for a certain period of time and not run or drip off of the hair, possibly causing eye or skin irritation. As such, the compositions may be in a cream, gel, foam, mousse, liquid, solid, powder, tonic, rinse, shampoo, spray, mascara, paste, or other suitable form.

The compositions of the present invention can be also be used as a pre-treatment or post-treatment step to additional coloring processes taking place in order to further enhance coloring performance or to create special and individualized coloring effects or to address specific needs of the consumer, e.g. roots or gray patches.

The compositions of the present invention can also be applied as leave-on (no further rinsing) or as rinse-off in which case a residence time on the hair to be bleaching and/or colored is required from about 30 seconds to about 2 hours, more preferably from about 1 minute to about 1 hour, even more preferably from about 5 minutes to about 40 minutes. These compositions may be applied as often as desired to achieve the desired color, shade, and intensity, i.e. a consumer does not have to wait several weeks prior to coloring again.

It is also contemplated that an additional component in the form of a sachet containing a powder comprising ammonium, sodium or potassium persulfate (to be applied by the consumer in an amount such that it would constitute about 5% of the final composition exposed to the hair to be bleaching and/or colored) may be used to further boost bleaching.

EXAMPLES

The following are non-limiting examples of the stable alkaline hair bleaching compositions of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified. As used herein, "minors" refers to those optional components such as preservatives, anti-oxidants, pH adjusters, viscosity modifiers, fragrances, and the like. As is apparent to one of ordinary skill in the art, the selection and quantity of these minors will vary depending on the physical and chemical characteristics of the particular ingredients selected to make the present invention as described herein.

In the examples above, water is used as the diluent. However in variations hereof water can be replaced, in part, by from about 0.5% to about 50% by weight of the total water content of the examples by diluents such as lower alcohols, e.g., ethylene glycol, ethylene glycol monoethyl ether, diethylene glycol, dipropyleneglycol, diethylene glycol monoethyl ether, propylene glycol, 1,3-propanediol, ethanol, isopropyl alcohol, glycerine, butoxyethanol, ethoxydiglycol, hexylene glycol, polyglyceryl-2-oleyl ether and mixtures thereof. Some pH adjusters are ammonium hydroxide, monoethanolamine and sodium hydroxide, although others may be substituted or used in place thereof.

| Example Number | 1 | 2 | 3 | 4 | 5 | 6 | 7 | 8 | 9 |
|---|---|---|---|---|---|---|---|---|---|
| hydrogen peroxide | 3 | 3 | 2 | 3 | 4.5 | 3 | 3 | 3 | 4.5 |
| pernanoic acid | — | — | 1 | — | — | — | — | 1 | — |
| disodium tetraborate decahydrate | 0.5 | 0.5 | 0.5 | 0.5 | 0.8 | 0.5 | 0.5 | 0.5 | 0.8 |
| cyclohexane-1,2-diamino-tetrakis phosphonic acid | 0.1 | 0.1 | 0.3 | 0.1 | 0.8 | 0.3 | 0.1 | 0.1 | 0.3 |
| sodium stannate | — | — | 0.05 | — | 0.05 | 0.05 | — | 0.05 | 0.05 |
| tetrasodium pyrophosphate | — | — | 0.1 | — | 0.1 | 0.1 | — | 0.1 | 0.1 |
| etidronic acid | — | — | 0.1 | — | 0.2 | 0.1 | — | 0.1 | 0.1 |
| sodium lauryl sulfate | — | 1 | — | — | — | 0.5 | — | — | 1 |
| $C_9$–$C_{11}$ Pareth-8 | — | — | 3 | 2 | 1 | 1 | — | — | 1 |
| PEG-2 hydrogenated tallow amine | — | 2 | — | — | 1 | — | — | 3 | 1 |
| alkyl dimethyl amine oxide | 0.3 | — | — | — | 1 | — | 0.3 | — | 0.5 |
| cocoamphoacetate | — | — | 1 | 1 | 0.5 | — | — | 0.5 | — |
| cocoamidopropylbetaine | — | — | 1 | — | — | 2 | — | 1 | — |
| copper sulfate | — | — | — | — | 0.5 | — | — | — | 0.5 |
| cetearyl alcohol | 5 | 5 | 7 | 5 | 3 | 4 | 5 | 4 | 4 |
| [1]hydrophobically modified nonionic polyol | — | 3 | — | 2 | 1 | — | — | 2 | — |
| [2]palmeth-60 hexyl dicarbamate | — | — | — | — | 2 | 4 | — | — | 2 |

-continued

| | | | | | | | | | |
|---|---|---|---|---|---|---|---|---|---|
| ³trimethylsilylamodimethicone | — | — | 2 | 0.5 | 3 | 5 | — | 3 | 5 |
| ⁴polyoxyethylene | — | — | 0.1 | 0.1 | 0.1 | — | — | 0.1 | — |
| HC Red No. 3 | — | — | — | — | — | — | 0.3 | 0.3 | 0.3 |
| HC Blue No. 2 | — | — | — | — | — | — | 0.1 | — | 0.3 |
| 5,6-dihydroxyindole | — | — | — | — | — | — | — | 1 | — |
| peroxidase | — | — | — | — | 0.1 | — | — | — | 0.1 |
| transglutaminase | — | — | — | — | — | 0.1 | — | 0.1 | — |
| Water and minors | to 100 | to 100 | to 100 | to 100 | to 100 | to 100 | to 100 | to 100 | to 100 |
| adjusted pH | 8.5 | 8.5 | 9 | 10 | 8.5 | 7 | 8.5 | 8 | 9 |

| Example Number | 10 | 11 | 12 | 13 | 14 | 15 | 16 | 17 | 18 |
|---|---|---|---|---|---|---|---|---|---|
| hydrogen peroxide | 3 | 3 | 4.5 | 4.5 | 3 | 3 | 3 | 3 | 4.5 |
| pernanoic acid | — | — | — | — | — | — | — | — | 0.3 |
| disodium tetraborate decahydrate | 0.5 | 0.5 | 0.5 | 0.5 | 0.8 | 0.5 | 0.5 | 0.5 | 0.8 |
| cyclohexane-1,2-diaminotetrakis phosphonic acid | 0.1 | 0.1 | 0.3 | 0.1 | 0.8 | 0.3 | 0.1 | 0.1 | 0.3 |
| sodium stannate | — | — | 0.05 | — | 0.05 | 0.05 | — | 0.05 | 0.05 |
| tetrasodium pyrophosphate | — | — | 0.1 | — | 0.1 | 0.1 | — | 0.1 | 0.1 |
| etidronic acid | — | — | 0.1 | — | 0.2 | 0.1 | — | 0.1 | 0.1 |
| sodium lauryl sulfate | — | 1 | — | — | — | 0.5 | — | — | 1 |
| C₉ to C₁₁ Pareth-8 | — | — | 3 | 2 | 1 | 1 | — | — | 1 |
| PEG-2 hydrogenated tallow amine | — | 2 | — | — | 1 | — | — | 3 | 1 |
| alkyl dimethyl amine oxide | 0.3 | — | — | — | 1 | — | 0.3 | — | 0.5 |
| cocoamphoacetate | — | — | 1 | 1 | 0.5 | — | — | 0.5 | — |
| cocoamidopropylbetaine | — | — | 1 | — | — | 2 | — | 1 | — |
| copper sulfate | — | — | — | — | 0.5 | — | — | — | 0.5 |
| cetearyl alcohol | 5 | 5 | 7 | 5 | 3 | 4 | 5 | 4 | 4 |
| ¹hydrophobically modified nonionic polyol | — | 3 | — | 2 | 1 | — | — | 2 | — |
| ²palmeth-60 hexyl dicarbamate | — | — | — | — | 2 | 4 | — | — | 2 |
| ³trimethylsilylamodimethicone | — | — | 2 | 0.5 | 3 | 5 | — | 3 | 5 |
| ⁴polyoxyethylene | — | — | 0.1 | 0.1 | 0.1 | — | — | 0.1 | — |
| p-phenylenediamine | — | — | — | 0.65 | 0.75 | — | 0.75 | 0.65 | 0.65 |
| toluene-diamine sulfate | 0.04 | — | 0.04 | — | — | — | — | — | — |
| p-aminophenol | 0.05 | 0.8 | 0.05 | 0.1 | 0.37 | — | 0.37 | 0.1 | 0.1 |
| 2,4,6,tetraaminopyrimidinium sulfate | — | — | — | — | — | 1.1 | — | — | — |
| m-phenylediamine | 0.03 | 0.1 | 0.03 | 0.24 | 0.4 | — | 0.4 | 0.24 | 0.24 |
| resorcinol | 0.004 | — | 0.004 | 0.05 | 0.2 | 0.13 | 0.2 | 0.05 | 0.05 |
| m-aminophenol | — | — | 0.01 | — | — | 0.05 | — | — | — |
| 2-amino-3 hydroxypyridine | 0.01 | — | — | 0.02 | — | — | — | 0.02 | 0.02 |
| 1-naphthol | — | 0.5 | — | — | 0.15 | — | 0.15 | — | — |
| 3-methyl-1-phenylpyrazolinone | — | — | — | — | — | — | — | — | 0.5 |
| N,N-dimethylacetoacetamide | — | — | — | — | — | — | — | — | 0.2 |
| HC Blue No. 2 | — | — | — | — | — | — | — | 0.05 | — |
| 5,6-dihydroxyindole | — | — | — | — | — | — | — | 1 | — |
| peroxidase | — | — | — | — | 0.1 | — | — | — | 0.1 |
| transglutaminase | — | — | — | — | — | 0.1 | — | 0.1 | — |
| Water and minors | to 100 | to 100 | to 100 | to 100 | to 100 | to 100 | to 100 | to 100 | to 100 |
| adjusted pH | 8.5 | 8.5 | 9 | 10 | 10 | 7 | 8.5 | 9 | 9 |

¹Aculyn ® 46, available from International Specialty Products.
²Elfacos ® T212 PPG-14, available from Azko Nober.
³Q2-8220, available from Dow Corning.
⁴Polyox ® 60K, available from Amerchol.

What is claimed is:

1. An alkaline hair bleaching composition comprising:
   (a) from about 0.01% to about 12%, by weight, of at least one oxidizing agent;
   (b) from about 0.2% to about 20%, by weight, of a buffering system, present in an amount sufficient to generate a pH of the composition in the range from about 5 to about 11, wherein said buffering system comprises at least one pH modifying ingredient selected from the group consisting of (i) borates buffers, (ii) alkalizing agents, and mixtures thereof;
   (c) from about 150 ppm to about 5,000 ppm of at least one stabilizer; and
   (d) from about 0.01% to about 50%, by weight, of at least one hair care ingredient selected from the group consisting of (i) surfactants, (ii) catalysts, (iii) thickeners, (iv) conditioners, and mixtures thereof.

2. A composition according to claim 1, comprising:
   (a) from about 1% to about 6%, by weight, of said oxidizing agent;
   (b) from about 0.1% to about 5%, by weight, of said borates buffer and from about 0.1% to about 15%, by weight, of said alkalizing agent;
   (c) from about 150 ppm to about 1,500 ppm of said stabilizer; and
   (d) from about 0.01% to about 30%, by weight, of said hair care ingredient.

3. A composition according to claim 1, wherein said oxidizing agent is an inorganic peroxygen oxidizing agent.

4. A composition according to claim 1, wherein said borates buffer is selected from the group consisting of ammonium borates, alkali metal borates and mixtures thereof; and said alkalizing agent is selected from the group consisting of ammonium hydroxide, ammonium carbonate, monoethanolamine, sodium hydroxide, ammonium hydrogen carbonate, and mixtures thereof.

5. A composition according to claim 1, wherein said stabilizer is selected from the group consisting of amino phosphates, nitriloacetates, hydroxyethyl-ethylene triamines, organic phosphates, alkali metal ethane-1-hydroxy diphosphonates, nitrilo trimethylene phosphonates, polycarboxylates, amino polycarboxylates polyphosphonates, amino polyphosphonates, aminomethylene phosphonic acids, water-soluble salts of aminomethylene phosphonic acid, and mixtures thereof.

6. A composition according to claim 1, wherein the pH of the composition is in the range from about 8 to about 10.

7. A composition according to claim 1, further comprising from about 0.001% to about 5%, by weight, of a hair coloring agent.

8. A composition according to claim 7, wherein said coloring agent is an oxidative coloring agent.

9. A composition according to claim 8, wherein said oxidative coloring agent is selected from the group consisting of p-phenylenediamine; m-phenylenediamine; o-phenylenediamine; p-aminophenol; m-aminophenol; o-aminophenol; m-diphenol; p-toluenediamine; 2-amino-3-hydroxy pyridine; heterocyclic amines; 2,4,5,6-tetraaminopyrimidine; 3-methyl-4-aminophenol; 2,6-dimethyl-p-phenylenediamine; 2-methyl-5-methoxy-p-phenylenediamine; 4-amino-N-methoxy-ethyl-aniline; 4-amino-N,N-ethyl-carbamylmethylaniline; 4-amino-N,N-di-β-hydroxyethylamine; pyrogallol; resorcinol; 4-amino-2-nitrophenol; nitro-p-phenylenediamine; N-phenyl-p-phenylenediamine; 2-amino-3-hydroxypyridine; 1-napthol; N,N-bis-(2-hydroxyethyl)-p-phenylenediamine; 4-amino-2-hydroxytoluene; 1,5-dihydroxynapthalene; 2-methyl resorcinol; 2,4-diaminoanisole; 4-amino-m-cresol; 2,4 diaminophenoxyethanol HCl; 3,4-methylenedioxyphenol; 1,7-dihydroxynaphthalene; 4-chlororesorcinol; 2,6-dihydroxy-3,4-dimethylpyridine; 1,3-bis-(2,4-diaminophenoxy) propane; 5-amino-6-chloro-o-cresol; 4-amino-2,6-dibromophenol; 4-amino-2,6-dichlorophenol; 1,3-dimethylpyrazolinone, 3-methyl-1-phenylpyrazolinone, 3-methylpyrazolinone, N,N-dimethylacetoacetamide, N,N-diethylacetoacetamide; 1,4-diamino-benzene; 2,5-diamino toluene; 2,5-diamino-anisole; 2,5-diamino-benzyl alcohol; 2-(2',5'-diamino)phenyl-ethanol; 5-amino-2-methyl phenol; 1,3-diamino-benzene; 1,3-diamino-benzene; 2,5-diamino-toluene, and mixtures thereof.

10. A composition according to claim 7, wherein said coloring agent is a non-oxidative coloring agent.

11. A composition according to claim 10, wherein said non-oxidative coloring agent is selected from the group consisting of nitro dyes; disperse dyes; azo dyes; anthraquinone dyes, naphthoquinone dyes; basic dyes; cat-ionic direct action dyes; metallized dyes; vat dyes; melanin-type dyes; and mixtures thereof.

12. A composition according to claim 10, wherein said non-oxidative coloring agent is selected from the group consisting of 5-N-(β-hydroxyethylamino)-2-methylphenol; nitroamino benzene; nitroaminophenol; nitroaryl amines; aminoanthraquinones; henna (*Lawsonia alba*) wherein the active ingredient is 2-hydroxy-1,4-naphtoquinone; chamomile (*Matricaria chamomila* or *Anthemis nobilis*) wherein the active ingredient is 4',5,7-trihydroxyflavone; indigo (Indigofera family); extracts of logwood, walnut hull, and nutgall; salts of silver, copper, nickel, bismuth, cobalt, and manganese; and mixtures thereof.

13. A composition according to claim 1, further comprising from about 0.0001% to about 5%, by weight, of at least one enzyme.

14. A composition according to claim 13, wherein said enzyme is selected from the group consisting of peroxidases, proteases, amylases, lipases, oxido-reductases, cutinases, esterases, cellulases, pectinases, lactases, and mixtures thereof.

15. A composition according to claim 14, wherein said enzyme is a laccase.

16. A method for bleaching human or animal hair comprising applying to the hair an effective amount of a composition according to claim 1.

17. A method for bleaching and coloring human or animal hair comprising applying to the hair an effective amount of a composition according to claim 7.

18. A method for bleaching and coloring human or animal hair comprising the steps of applying to the hair a first component followed by applying a second component, wherein the first component comprises a composition according to claim 1, and the second component comprises a hair coloring agent.

19. A hair bleaching and coloring kit comprising at least two components, a first component comprising a hair bleaching composition according to claim 1, and a second component comprising a hair coloring agent.

20. An alkaline hair bleaching composition comprising:
 (a) from about 1% to about 6%, by weight, of an inorganic peroxygen oxidizing agent;
 (b) from about 0.2% to about 20%, by weight, of a buffering system, present in an amount sufficient to generate a pH of the composition in the range from about 5 to about 11, wherein said buffering system comprises:
  (i) from about 0.1% to about 5%, by weight, of a borates buffer selected from the group consisting of ammonium borates, alkali metal borates, and mixtures thereof; and
  (ii) from about 0.1% to about 15%, by weight, of an alkalizing agent selected from the group consisting of ammonium hydroxide, ammonium carbonate, monoethanolamine, sodium hydroxide, ammonium hydrogen carbonate, and mixtures thereof;
 (c) from about 150 ppm to about 1,500 ppm of at least one stabilizer selected from the group consisting of aminomethylene phosphonic acids, water-soluble salts of aminomethylene phosphonic acids, and mixtures thereof; and
 (d) from about 0.01% to about 30%, by weight, of at least one hair care ingredient selected from the group consisting of (i) surfactants, (ii) catalysts, (iii) thickeners, (iv) conditioners, and mixtures thereof.

* * * * *